United States Patent
Lu et al.

(10) Patent No.: US 12,083,161 B2
(45) Date of Patent: *Sep. 10, 2024

(54) TREATING IgE-MEDIATED ALLERGIC DISEASES

(71) Applicant: Oneness Biotech Co., Ltd., Taipei (TW)

(72) Inventors: Kung-Ming Lu, Taipei (TW); Nien-Yi Chen, Taipei (TW); Tien-Tien Cheng, Taipei (TW)

(73) Assignee: ONENESS BIOTECH CO., LTD., Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 17/930,799

(22) Filed: Sep. 9, 2022

(65) Prior Publication Data

US 2023/0100100 A1  Mar. 30, 2023

Related U.S. Application Data

(63) Continuation of application No. 16/862,512, filed on Apr. 29, 2020, now Pat. No. 11,439,682, which is a continuation-in-part of application No. PCT/CN2018/112714, filed on Oct. 30, 2018.

(60) Provisional application No. 62/579,416, filed on Oct. 31, 2017.

(51) Int. Cl.
*A61K 31/56* (2006.01)
*A61K 9/00* (2006.01)
*A61K 38/17* (2006.01)
*A61P 17/04* (2006.01)

(52) U.S. Cl.
CPC ........ *A61K 38/1774* (2013.01); *A61K 9/0014* (2013.01); *A61K 9/0019* (2013.01); *A61K 31/56* (2013.01); *A61P 17/04* (2018.01)

(58) Field of Classification Search
CPC .............. A61K 38/1774; A61K 9/0014; A61K 9/0019; A61K 31/56; A61P 17/04
See application file for complete search history.

(56) References Cited

U.S. PATENT DOCUMENTS

| | | |
|---|---|---|
| 5,079,344 A | 1/1992 | Chang et al. |
| 5,089,603 A | 2/1992 | Chang |
| 5,091,313 A | 2/1992 | Chang |
| 5,231,026 A | 7/1993 | Chang |
| 5,252,467 A | 10/1993 | Chang |
| 5,254,671 A | 10/1993 | Chang |
| 5,260,416 A | 11/1993 | Chang |
| 5,274,075 A | 12/1993 | Chang |
| 5,281,699 A | 1/1994 | Chang |
| 5,292,867 A | 3/1994 | Chang |
| 5,298,420 A | 3/1994 | Chang |
| 5,310,875 A | 5/1994 | Chang |
| 5,342,924 A | 8/1994 | Chang |
| 5,362,643 A | 11/1994 | Chang |
| 5,420,251 A | 5/1995 | Chang et al. |
| 5,422,258 A | 6/1995 | Chang |
| 5,449,760 A | 9/1995 | Chang |
| 5,484,907 A | 1/1996 | Chang et al. |
| 5,514,776 A | 5/1996 | Chang |
| 5,543,144 A | 8/1996 | Chang |
| 5,601,821 A | 2/1997 | Stanworth et al. |
| 5,614,611 A | 3/1997 | Chang |
| 5,653,980 A | 8/1997 | Hellman |
| 5,690,934 A | 11/1997 | Chang et al. |
| 5,866,129 A | 2/1999 | Chang et al. |
| 6,887,472 B2 | 5/2005 | Morsey et al. |
| 7,897,151 B2 | 3/2011 | Morsey et al. |
| 8,071,097 B2 | 12/2011 | Wu et al. |
| 8,137,670 B2 | 3/2012 | Wu et al. |
| 8,460,664 B2 | 6/2013 | Chang et al. |
| 8,741,294 B2 | 6/2014 | Chang et al. |
| 2009/0010924 A1 | 1/2009 | Wu et al. |
| 2009/0220416 A1 | 9/2009 | Welt et al. |
| 2012/0207746 A1 | 8/2012 | Chang et al. |
| 2013/0034554 A1 | 2/2013 | Garcia-Martinez et al. |
| 2014/0072583 A1 | 3/2014 | Ardeleanu et al. |
| 2015/0086558 A1 | 3/2015 | Chang et al. |

FOREIGN PATENT DOCUMENTS

| | | |
|---|---|---|
| JP | 2015-221820 A | 12/2015 |
| WO | WO 89/06138 A1 | 7/1989 |
| WO | WO 90/15614 A1 | 12/1990 |
| WO | WO 91/04055 A1 | 4/1991 |
| WO | WO 91/11456 A1 | 8/1991 |
| WO | WO 92/07574 A1 | 5/1992 |
| WO | WO 96/12740 A1 | 5/1996 |
| WO | WO 98/53843 A1 | 12/1998 |
| WO | WO 03/086348 A1 | 10/2003 |
| WO | WO 2007/041171 A2 | 4/2007 |

(Continued)

OTHER PUBLICATIONS

[No Author Listed], GenBank Accession No. AER46505.1, Kuwata, Nov. 6, 2011, 2 pages.
[No Author Listed], GenBank Accession No. BAE71466.1, Furukawa et al., Jan. 6, 2006, 2 pages.
[No Author Listed], GenBank Accession No. S17626, Clackson et al., Jan. 21, 2000, 2 pages.
[No Author Listed], GenBank Accession No. S45714, Kim et al., May 7, 1999, 3 pages.
Achatz et al., Membrane bound IgE: the key receptor to restrict high IgE levels. Open Immunology Journal. 2008;1:25-32.
Batista et al., Characterization and expression of alternatively spliced IgE heavy chain transcripts produced by peripheral blood lymphocytes. J Immunol. Jan. 1, 1995;154(1):209-18.

(Continued)

*Primary Examiner* — Julie Ha
*Assistant Examiner* — Kristina M Hellman
(74) *Attorney, Agent, or Firm* — Mintz, Levin, Cohn, Ferris, Glovsky and Popeo, P.C.

(57) ABSTRACT

Methods for treating a disorder associated with immunoglobulin E (IgE) in a subject with antibodies capable of binding to the Cεmx domain of a membrane-bound IgE. The subject can be administered with at least two doses of the antibody, the two doses being at least three months apart.

17 Claims, 8 Drawing Sheets

Specification includes a Sequence Listing.

(56) References Cited

FOREIGN PATENT DOCUMENTS

| WO | WO 2007/131129 A2 | 11/2007 |
|---|---|---|
| WO | WO 2008/116149 A2 | 9/2008 |
| WO | WO 2010/097012 A1 | 9/2010 |
| WO | WO 2011/108008 A2 | 9/2011 |

OTHER PUBLICATIONS

Batista et al., Characterization of the human immunoglobulin epsilon mRNAs and their polyadenylation sites. Nucleic Acids Res. Dec. 11, 1995;23(23):4805-11.
Batista et al., The two membrane isoforms of human IgE assemble into functionally distinct B cell antigen receptors. J Exp Med. Dec. 1, 1996;184(6):2197-205.
Benhamou et al., Anti-immunoglobulins induce death by apoptosis in WEHI-231 B lymphoma cells. Eur J Immunol. Jun. 1990;20(6):1405-7.
Berard et al., Activation sensitizes human memory B cells to B-cell receptor-induced apoptosis. Immunology. Sep. 1999;98(1):47-54.
Bozelka et al., IgE isotype suppression in anti-epsilon-treated mice. Immunology. Jul. 1982;46(3):527-32.
Brightbill et al., Antibodies specific for a segment of human membrane IgE deplete IgE-producing B cells in humanized mice. J Clin Invest. Jun. 2010;120(6):2218-29.
Boguniewicz et al., Current management of atopic dermatitis and interruption of the atopic march. J Allergy Clin Immunol. Dec. 2003;112(6 Suppl):S140-50.
Caraux et al., Surface immunoglobulins as targets for anti-immunoglobulin-dependent cell-mediated lysis of B cells. Cell Immunol. Mar. 1983;76(2):372-8.
Chan et al., The novel human IgE epsilon heavy chain, epsilon tailpiece, is present in plasma as part of a covalent complex. Mol Immunol. Apr. 2000;37(5):241-52.
Chang et al., Anti-IgE antibodies for the treatment of IgE-mediated allergic diseases. Adv Immunol. 2007;93:63-119.
Chang et al., Monoclonal antibodies specific for human IgE-producing B cells: a potential therapeutic for IgE-mediated allergic diseases. Biotechnology (N Y). Feb. 1990;8(2):122-6.
Chang, Developing antibodies for targeting immunoglobulin and membrane-bound immunoglobulin E. Allergy Asthma Proc. Mar.-Apr. 2006;27(2 Suppl 1):S7-14.
Chang, The pharmacological basis of anti-IgE therapy. Nat Biotechnol. Feb. 2000;18(2):157-62.
Chen et al., Monoclonal antibodies against the C(epsilon)mX domain of human membrane-bound IgE and their potential use for targeting IgE-expressing B cells. Int Arch Allergy Immunol. Aug. 2002;128(4):315-24.
Chen et al., Unique epitopes on C epsilon mX in IgE-B cell receptors are potentially applicable for targeting IgE-committed B cells. J Immunol. Feb. 15, 2010;184(4):1748-56. Epub Jan. 18, 2010.
Chinn et al., Antibody therapy of non-Hodgkin's B-cell lymphoma. Cancer Immunol Immunother. May 2003;52(5):257-80. Epub Feb. 28, 2003.
Chowdhury et al., Targeting the junction of CεmX and ε-migis for the specific depletion of mIgE-expressing B cells. Mol Immunol. Oct. 2012; 52(3-4):279-88. Epub Jun. 29, 2012.
Davis et al., An epitope on membrane-bound but not secreted IgE: implications in isotype-specific regulation. Biotechnology (N Y). Jan. 1991;9(1):53-6.
Davis et al., Can anti-IgE be used to treat allergy? Springer Semin Immunopathol. 1993;15(1):51-73.
Delves, Allergic Rhinitis. Merck Manual. 1-6. Accessed Nov. 2, 2017.
Disis et al., Granulocyte-macrophage colony-stimulating factor: an effective adjuvant for protein and peptide-based vaccines. Blood. Jul. 1, 1996;88(1):202-10.
Donjerković et al., Activation-induced cell death in B lymphocytes. Cell Res. Sep. 2000;10(3):179-92.

Fernandez, Hyper-IgE Syndrome. Merck Manual. 1-2. Merckmanuals.com/professional/immunology-allergic-disorders/immunodeficiency-disorders/hyper-ige-syndrome?query=hyper ige syndrome. Accessed Nov. 20, 2021.
Eray et al., Cross-linking of surface IgG induces apoptosis in a bcl-2 expressing human follicular lymphoma line of mature B cell phenotype. Int Immunol. Dec. 1994;6(12):1817-27.
Ezzo, Treatment and managed care issues of atopic dermatitis. Am J Manag Care. Jun. 2017;23(8 Suppl):S124-S131.
Feichtner et al., Targeting the extracellular membrane-proximal domain of membrane-bound IgE by passive immunization blocks IgE synthesis in vivo. J Immunol. Apr. 15, 2008;180(8):5499-505.
Grafton et al., Mechanisms of antigen receptor-dependent apoptosis of human B lymphoma cells probed with a panel of 27 monoclonal antibodies. Cell Immunol. Nov. 25, 1997;182(1):45-56.
Haak-Frendscho et al., Administration of an anti-IgE antibody inhibits CD23 expression and IgE production in vivo. Immunology. Jun. 1994;82(2):306-13.
Haba et al., Inhibition of IgE synthesis by anti-IgE: role in long-term inhibition of IgE synthesis by neonatally administered soluble IgE. Proc Natl Acad Sci U S A. May 1990;87(9):3363-7.
Hung et al., Alleles and isoforms of human membrane-bound IgA1. Mol Immunol. Aug. 2008;45(13):3624-30. Epub Jun. 6, 2008.
Inführ et al., Molecular and cellular targets of anti-IgE antibodies. Allergy. Aug. 2005;60(8):977-85.
Iyengar et al., Immunologic effects of omalizumab in children with severe refractory atopic dermatitis: a randomized, placebo-controlled clinical trial. Int Arch Allergy Immunol. 2013;162(1):89-93. Epub Jun. 27, 2013.
Janeway et al., Immunobiology: the immune system in health and disease. 6$^{th}$ edition. 2005:352-353, 401-402.
Janeway et al., Part II: The Recognition of Antigen, Chapter 3: Structure of the Antibody Molecule and Immunoglobulin Genes. Immunobiology: the immune system in health and disease. 1997. 14 pages.
Jorgensen et al., Recent trends in stabilising peptides and proteins in pharmaceutical formulation—considerations in the choice of excipients. Expert Opin Drug Deliv. Nov. 2009;6(11):1219-30.
Kass et al., Induction of protective host immunity to carcinoembryonic antigen (CEA), a self-antigen in CEA transgenic mice, by immunizing with a recombinant vaccinia-CEA virus. Cancer Res. Feb. 1, 1999;59(3):676-83.
Lin et al., CεmX peptide-carrying HBcAg virus-like particles induced antibodies that down-regulate mIgE-B lymphocytes. Mol Immunol. Oct. 2012;52(3-4):190-9.
Liour et al., Treating IgE-mediated diseases via targeting IgE-expressing B cells using an anti-CεmX antibody. Pediatr Allergy Immunol. Aug. 2016;27(5):446-51. Epub May 18, 2016.
Lorenzi et al., Sequence-specific antibodies against human IgE isoforms induced by an epitope display system. Immunotechnology. Mar. 1999;4(3-4):267-72.
Lyczak et al., Expression of novel secreted isoforms of human immunoglobulin E proteins. J Biol Chem. Feb. 16, 1996;271(7):3428-36.
MacGlashan, IgE-dependent signaling as a therapeutic target for allergies. Trends Pharmacol Sci. Sep. 2012;33(9):502-9. Epub Jun. 30, 2012.
Major et al., Structural features of the extracellular portion of membrane-anchoring peptides on membrane-bound immunoglobulins. Mol Immunol. Feb. 1996;33(2):179-87.
Martin et al., B cell immunobiology in disease: evolving concepts from the clinic. Annu Rev Immunol. 2006;24:467-96.
Mathas et al., Anti-CD20- and B-cell receptor-mediated apoptosis: evidence for shared intracellular signaling pathways. Cancer Res. Dec. 15, 2000;60(24):7170-6.
Ortega et al., Asthma. Merck Manual. 1-19. Accessed Nov. 2, 2017.
Parry et al., Hypercross-linking surface IgM or IgD receptors on mature B cells induces apoptosis that is reversed by costimulation with IL-4 and anti-CD40. J Immunol. Mar. 15, 1994;152(6):2821-9.
Peng et al., A new isoform of human membrane-bound IgE. J Immunol. Jan. 1, 1992;148(1):129-36.

(56) References Cited

OTHER PUBLICATIONS

Poggianella et al., The extracellular membrane-proximal domain of human membrane IgE controls apoptotic signaling of the B cell receptor in the mature B cell line A20. J Immunol. Sep. 15, 2006;177(6):3597-605.
Takamuku et al., Apoptosis in antibody-dependent monocyte-mediated cytotoxicity with monoclonal antibody 17-1A against human colorectal carcinoma cells: enhancement with interferon gamma. Cancer Immunol Immunother. Dec. 1996;43(4):220-5.
Talay et al., IgE+ memory B cells and plasma cells generated through a germinal-center pathway. Nat Immunol. Feb. 26, 2012;13(4):396-404.
Timmerman, Linkage of foreign carrier protein to a self-tumor antigen enhances the immunogenicity of a pulsed dendritic cell vaccine. J Immunol. May 1, 2000;164(9):4797-803.
Tyagi et al., Chemical modification and chemical cross-linking for protein/enzyme stabilization. Biochemistry (Mosc). Mar. 1998;63(3):395-407.
Wagner et al., Monoclonal anti-equine IgE antibodies with specificity for different epitopes on the immunoglobulin heavy chain of native IgE, Veterinary Immunology and Immunopathology. 2003;92(1):45-60.
Walling et al., Update on the management of chronic eczema: new approaches and emerging treatment options. Clin Cosmet Investig Dermatol. Jul. 28, 2010;3:99-117.
Wan et al., Genetic variations in the C epsilon mX domain of human membrane-bound IgE. Immunogenetics. May 2010;62(5):273-80. Epub Mar. 24, 2010.
Yu et al., Two isoforms of human membrane-bound alpha Ig resulting from alternative mRNA splicing in the membrane segment. J Immunol. Dec. 1, 1990;145(11):3932-6.
Zellweger et al., IgE-associated allergic disorders: recent advances in etiology, diagnosis, and treatment. Allergy. Dec. 2016;71(12):1652-1661.
Zhang et al., Complex alternative RNA splicing of epsilon-immunoglobulin transcripts produces mRNAs encoding four potential secreted protein isoforms. J Biol Chem. Jan. 7, 1994;269(1):456-62.
Zhang et al., Two unusual forms of human immunoglobulin E encoded by alternative RNA splicing of epsilon heavy chain membrane exons. J Exp Med. Jul. 1, 1992;176(1):233-43.
Chan et al., "Developing an antibody targeting CemX of mIgE for the treatment of allergic and other IgE-mediated diseases (VAC6P. 954)", J Immunol (2014) 192 (1_Supplement): 140.15.
Uchiyama, "Liquid formulation for antibody drugs", Biochimica et Biophysica Acta (BBA)—Proteins and Proteomics vol. 1844, Issue 11, Nov. 2014, pp. 2041-2052.

```
Heavy chain
             1         10        20        30        40        50        60
4B12   DVQLQESGPGLVKPSQSLSLTCTVTGYSITSDYAWNWIRQFPGNKLEWMGSISYSGITGYNPSLKS
FB825  QVQLQESGPGLVKPSETLSLTCTVSGYSITSDYAWNWIRQPPGKGLEWIGSISYSGITGYNPSLKS 70        80        90        100
4B12   RISVTRDTSKNQFFLQLNSVTTEDTATYYCARMGYDGLAYWGHGTTVTVSA    (SEQ ID NO:4)
FB825  RVTISVDTSKNQFSLKLSSVTAADTAVYYCARMGYDGLAYWGQGTLVTVSS    (SEQ ID NO:2)

Light chain
             1         10        20        30        40        50        60
4B12   DVLMTQTPLSLPVSLGDQASISCRSSQSIVHSNGNTYLEWYLQKPGQSPKLLIYKVSNRFSGVPD
FB825  DIVMTQTPLSLSVTPGQPASISCRSSQSIVHSNGNTYLEWYLQKPGQSPQLLIYKVSNRFSGVPD 70        80        90        100
4B12   RFSGSGSGTEFTFKISRVEAEDLGVYYCFQGSHVPPTFGGGTKLEIKR    (SEQ ID NO:5)
FB825  RFSGSGSGTEFTLKISRVEAEDVGVYYCFQGSHVPPTFGGGTKVEIKR    (SEQ ID NO:3)
```

Fig. 4

SEQUENCE LISTING

```
Sequence total quantity: 12
SEQ ID NO: 1              moltype = AA   length = 17
FEATURE                   Location/Qualifiers
REGION                    1..17
                          note = SYNTHESIZED
source                    1..17
                          mol_type = protein
                          organism = synthetic construct
SEQUENCE: 1
GLAGGSAQSQ RAPDRVL                                                    17

SEQ ID NO: 2              moltype = AA   length = 117
FEATURE                   Location/Qualifiers
REGION                    1..117
                          note = SYNTHESIZED
source                    1..117
                          mol_type = protein
                          organism = synthetic construct
SEQUENCE: 2
QVQLQESGPG LVKPSETLSL TCTVSGYSIT SDYAWNWIRQ PPGKGLEWIG SISYSGITGY     60
NPSLKSRVTI SVDTSKNQFS LKLSSVTAAD TAVYYCARMG YDGLAYWGQG TLVTVSS        117

SEQ ID NO: 3              moltype = AA   length = 113
FEATURE                   Location/Qualifiers
REGION                    1..113
                          note = SYNTHESIZED
source                    1..113
                          mol_type = protein
                          organism = synthetic construct
SEQUENCE: 3
DIVMTQTPLS LSVTPGQPAS ISCRSSQSIV HSNGNTYLEW YLQKPGQSPQ LLIYKVSNRF     60
SGVPDRFSGS GSGTEFTLKI SRVEAEDVGV YYCFQGSHVP PTFGGGTKVE IKR            113

SEQ ID NO: 4              moltype = AA   length = 117
FEATURE                   Location/Qualifiers
REGION                    1..117
                          note = SYNTHESIZED
source                    1..117
                          mol_type = protein
                          organism = synthetic construct
SEQUENCE: 4
DVQLQESGPG LVKPSQSLSL TCTVTGYSIT SDYAWNWIRQ FPGNKLEWMG SISYSGITGY     60
NPSLKSRISV TRDTSKNQFF LQLNSVTTED TATYYCARMG YDGLAYWGHG TTVTVSA        117

SEQ ID NO: 5              moltype = AA   length = 113
FEATURE                   Location/Qualifiers
REGION                    1..113
                          note = SYNTHESIZED
source                    1..113
                          mol_type = protein
                          organism = synthetic construct
SEQUENCE: 5
DVLMTQTPLS LPVSLGDQAS ISCRSSQSIV HSNGNTYLEW YLQKPGQSPK LLIYKVSNRF     60
SGVPDRFSGS GSGTEFTFKI SRVEAEDLGV YYCFQGSHVP PTFGGGTKLE IKR            113

SEQ ID NO: 6              moltype = AA   length = 52
FEATURE                   Location/Qualifiers
REGION                    1..52
                          note = SYNTHESIZED
source                    1..52
                          mol_type = protein
                          organism = synthetic construct
SEQUENCE: 6
GLAGGSAQSQ RAPDRVLCHS GQQQGLPRAA GGSVPHPRCH CGAGRADWPG PP             52

SEQ ID NO: 7              moltype = AA   length = 12
FEATURE                   Location/Qualifiers
REGION                    1..12
                          note = SYNTHESIZED
source                    1..12
                          mol_type = protein
                          organism = synthetic construct
SEQUENCE: 7
GLAGGSAQSQ RA                                                         12

SEQ ID NO: 8              moltype = AA   length = 117
FEATURE                   Location/Qualifiers
REGION                    1..117
```

```
                        note = SYNTHESIZED
source                  1..117
                        mol_type = protein
                        organism = synthetic construct
SEQUENCE: 8
QVQLQESGPG LVKPSETLSL TCTVSGYSIT SDYAWNWIRQ PPGKGLEWMI SISYSGITGY   60
NPSLKSRVTI SVDTSKNQFS LKLSSVTAAD TAVYYCARMG YDGLAYWGQG TLVTVSS     117

SEQ ID NO: 9            moltype = AA   length = 117
FEATURE                 Location/Qualifiers
REGION                  1..117
                        note = SYNTHESIZED
source                  1..117
                        mol_type = protein
                        organism = synthetic construct
SEQUENCE: 9
QVQLQESGPG LVKPSETLSL TCTVSGYSIT SDYAWNWIRQ PPGKGLEWIG SISYSGITGY   60
NPSLKSRVTI SRDTSKNQFS LKLSSVTAAD TAVYYCARMG YDGLAYWGQG TLVTVSS     117

SEQ ID NO: 10           moltype = AA   length = 113
FEATURE                 Location/Qualifiers
REGION                  1..113
                        note = SYNTHESIZED
source                  1..113
                        mol_type = protein
                        organism = synthetic construct
SEQUENCE: 10
DIVMTQTPLS LSVTPGQPAS ISCRSSQSIV HSNGNTYLEW YLQKPGQSPQ LLIYKVSNRF   60
SGVPDRFSGS GSGTDFTLKI SRVEAEDVGV YYCFQGSHVP PTFGGGTKVE IKR         113

SEQ ID NO: 11           moltype = AA   length = 466
FEATURE                 Location/Qualifiers
REGION                  1..466
                        note = SYNTHESIZED
source                  1..466
                        mol_type = protein
                        organism = synthetic construct
SEQUENCE: 11
MEFGLSWLFL VAILKGVQCQ VQLQESGPGL VKPSETLSLT CTVSGYSITS DYAWNWIRQP   60
PGKGLEWIGS ISYSGITGYN PSLKSRVTIS RDTSKNQFSL KLSSVTAADT AVYYCARMGY  120
DGLAYWGQGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSCD  240
KTHTCPPCPA PELLGGPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPSRDELTKN QVSLTCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 12           moltype = AA   length = 239
FEATURE                 Location/Qualifiers
REGION                  1..239
                        note = SYNTHESIZED
source                  1..239
                        mol_type = protein
                        organism = synthetic construct
SEQUENCE: 12
MRVPAQLLGL LLLWLPGARC DIVMTQTPLS LSVTPGQPAS ISCRSSQSIV HSNGNTYLEW   60
YLQKPGQSPQ LLIYKVSNRF SGVPDRFSGS GSGTDFTLKI SRVEAEDVGV YYCFQGSHVP  120
PTFGGGTKVE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239
```

TREATING IgE-MEDIATED ALLERGIC DISEASES

RELATED APPLICATION

This application is a continuation of U.S. application Ser. No. 16/862,512, filed Apr. 29, 2020, which is a continuation-in-part of International Patent Application No. PCT/CN2018/112714, filed on Oct. 30, 2018, which claims the benefit of the filing date under 35 U.S.C. § 119 of U.S. Provisional Application Ser. No. 62/579,416, filed Oct. 31, 2017, the entire contents of each of which are incorporated by reference herein.

SEQUENCE LISTING

The application contains a Sequence Listing that has been filed electronically in the form of an XML file, created Sep. 9, 2022, and named "112127-0151_Sequence_Listing.xml" (17,378 bytes), the contents of which are incorporated by reference herein in their entirety.

BACKGROUND OF THE INVENTION

IgE plays a central role in mediating type I hypersensitivity reactions that are responsible for causing allergic diseases, including allergic asthma, allergic rhinitis, atopic dermatitis, and others. Allergic reactions are the responses of the immune system toward harmless environmental substances, such as dust mites, tree and grass pollens, certain food and drugs, and bee and fire ant bites. In such reactions, the binding of an allergen to IgE on the surface of basophils and mast cells causes the cross-linking of IgE and the aggregation of the underlying receptors of IgE.Fc, the type I IgE.Fc receptors, or FcεRI. This receptor aggregation subsequently activates the signaling pathway leading to the exocytosis of granules and the release of pharmacologic mediators, such as histamine, leukotrienes, tryptase, cytokines and chemokines. The release of those mediators from mast cells and basophils causes the various pathological manifestations of allergy.

There are two types of IgE molecules, free (or soluble) IgE and membrane-bound IgE (mIgE). Free IgE molecules circulate in the blood and interstitial fluid. mIgE are expressed on the surface of B lymphoblasts and memory B cells. Targeting mIgE is believed to be effective in inhibiting the production of antigen-specific IgE and thus suppressing IgE-medicated immune responses.

SUMMARY OF THE INVENTION

The present disclosure is based on the unexpected discovery that a single dose of FB825, an antibody that targets the CεmX domain of mIgE on human B lymphocytic cells, successfully reduced the level of total IgE in human subjects for at least three months.

Accordingly, one aspect of the present disclosure provides a method for treating a disorder associated with IgE, the method comprising administering to a subject in need thereof a first dose of an antibody binding to a Cεmx domain of a membrane-bound IgE; and administering to the subject a second dose of the antibody. The second dose is administered at least 8 weeks (e.g., at least 10 weeks, 12 weeks or 3 months) after the first dose.

In any of the methods described herein, the first dose, the second dose, or both may range from 0.5 mg/kg to 15 mg/kg (e.g., 1 mg/kg to 15 mg/kg). For example, the first dose, the second dose, or both range from 1 mg/kg to 8 mg/kg (e.g., 1.5 mg/kg to 10 mg/kg). The first dose, the second dose, or both can be administered by intravenous injection.

The subject to be treated by the method described herein may be a human patient having or suspected of having the disorder associated with IgE, e.g., allergic asthma, allergic rhinitis, hyper IgE syndrome, or atopic dermatitis. In some embodiments, the disorder is cold-induced urticaria, chronic urticaria, cholinergic urticaria, chronic rhinosinusitis, systemic mastocytosis, cutaneous mastocytosis, allergic bronchopulmonary aspergillosis, recurrent idiopathic angioedema, and interstitial cystitis, eosinophil-associated gastrointestinal disorders, a food allergy, or a drug allergy.

In another aspect, the present disclosure provides a method of treating atopic dermatitis, the method comprising administering to a subject in need thereof a first dose of an antibody binding to a Cεmx domain of a membrane-bound IgE; wherein the first dose is about 1 mg/kg to 10 mg/kg (e.g., 3 mg/kg to 8 mg/kg, e.g., 5 mg/kg). The method may further comprise administering to the subject a second dose of the antibody about 3 months after the first dose, if at the time of the second dose, the change of the total IgE level in the subject from the total IgE level before the first dose is less than 50%. In some instances, the second dose may be identical to the first dose, e.g., 5 mg/kg. The first dose of the antibody, the second dose of the antibody, or both may be administered by intravenous infusion.

In any of the method described above, a moisturizer is applied to the subject at least twice a day for at least seven consecutive days prior to the first dose. Alternatively or in addition, the method may further comprise administering to the subject a topical corticosteroid. In some instances, the topical corticosteroid is applied to an active lesion daily. Such a topical corticosteroid may be a 0.05% fluticasone propionate cream, a 0.1% monetasone furoate cream, a 0.06% betamethasone valerate, or a 1% hydrocortisone ointment. In other instances, the topical corticosteroid may be a 0.05% fluocinonide cream, a 0.25% desoximetasone ointment, or a 0.05% clobetasol propionate ointment.

In some embodiments, the subject is free of topical tacrolimus treatment, topical pimecrolimus treatment, systemic corticosteroid treatment, leukotriene inhibitor treatment, allergen immunotherapy, a treatment involving an immunosuppressive or immunomodulating agent, vaccine treatment, a treatment involving a traditional Chinese medicine, a surgical procedure, an ultraviolet procedure, or tanning.

In any of the treatment methods described herein, the anti-CεmX antibody described herein may bind the mIgE fragment GLAGGSAQSQRAPDRVL (SEQ ID NO:1) or the mIgE fragment GLAGGSAQSQRA (SEQ ID NO:7). In some instances, the antibody binds to the same epitope as antibody 4B12 (FB825) or competes against antibody FB825 from binding to the Cεmx domain of a membrane-bound IgE. In some examples, the antibody comprises the same heavy chain complementary determining regions as antibody FB825 and/or the same light chain complementary determining regions as antibody FB825. Such an antibody may be a humanized antibody of 4B12, for example, FB825. The antibody may comprise a heavy chain variable region having the amino acid sequence of SEQ ID NO: 2, SEQ ID NO:8, or SEQ ID NO:9; and/or a light chain variable region having the amino acid sequence of SEQ ID NO: 3 or SEQ ID NO:10. Any of the antibodies used in any of the methods described herein can be full-length antibody or an antigen-binding fragment thereof. The antibody can be a human antibody, a humanized antibody, a chimeric antibody, or a single-chain antibody. In some embodiments, the antibody can be an IgG1 molecule. In specific examples, the antibody may comprise a heavy chain of SEQ ID NO:11 and a light chain of SEQ ID NO:12 (with or without the signal peptide in both sequences).

In any of the methods described herein, the anti-CεmX antibody can be formulated in a pharmaceutical composition comprising the antibody, a buffer (e.g., a buffer comprising an amino acid such as histidine), a salt (e.g., sodium chloride), and a nonionic surfactant (e.g., polysorbate 80). In some embodiments, the pharmaceutical composition is an aqueous solution having a pH of 5 to 8. In some examples, the antibody in the pharmaceutical composition is about 10 mg/ml to 30 mg/ml (e.g., about 20 mg/ml), the histidine buffer is of a concentration of about 10-30 mM (e.g., about 20 mM), the sodium chloride is of a concentration of about 120-160 mM (e.g., about 140 mM), and the polysorbate 80 is of a concentration of about 0.01-0.03% (e.g., about 0.02%). Any of the pharmaceutical compositions described herein is also within the scope of the present disclosure.

In another aspect, provided herein is an aqueous formulation, comprising any of the anti-CεmX antibody described herein (e.g., FB825 or a functional variant thereof) at a concentration about 10 mg/ml to 30 mg/ml, a buffer comprising an amino acid (e.g., histidine) at a concentration of about 10-30 mM, a salt (e.g., sodium chloride) at a concentration of about 120-160 mM, and a nonionic surfactant (e.g., polysorbate 80) at a concentration of about 0.01-0.03%, wherein the aqueous formulation has a pH of about 5-8. In one example, the aqueous formulation comprises the antibody is at a concentration of about 20 mg/ml, the histidine buffer is at a concentration of about 20 mM, the sodium chloride is at a concentration of about 140 mM, and the polysorbate 80 is at a concentration of about 0.02%, and wherein the aqueous formulation has a pH of about 6.5.

Also within the scope of the present disclosure are (i) a pharmaceutical composition for use in treating IgE-associated disorders as described herein, wherein the pharmaceutical composition comprises an anti-CεmX antibody and a pharmaceutically acceptable carrier, and wherein the pharmaceutical composition is administered to a subject in need of the treatment for at least two doses, which are at least 8 weeks (e.g., at least 10 weeks, 12 weeks, or three months apart, or 12 weeks to 6 months apart); and (ii) uses of the anti-CεmX antibody in manufacturing a medicament for use in treating the IgE-associated disorder, wherein the medicament can be administered to a subject in need of the treatment for at least two doses, which are at least three months apart.

The details of one or more embodiments of the invention are set forth in the description below. Other features or advantages of the present invention will be apparent from the following drawings and detailed description of several embodiments, and also form the appended claims.

BRIEF DESCRIPTION OF THE DRAWINGS

FIG. 4 shows the amino acid sequence alignment of the $V_H$ and $V_L$ of monoclonal antibody 4B12 and monoclonal antibody FB825, which is a humanized 4B12 antibody. Variations between the two antibodies are highlighted. The $V_H$ and $V_L$ complementary determining regions (CDRs) are in boldface and underlined. $V_H$ of 4B12: SEQ ID NO:4. $V_L$ of 4B12: SEQ ID NO:5. $V_H$ of FB825: SEQ ID NO:2. $V_L$ of FB825: SEQ ID NO:3.

DETAILED DESCRIPTION OF THE INVENTION

Figure 1:
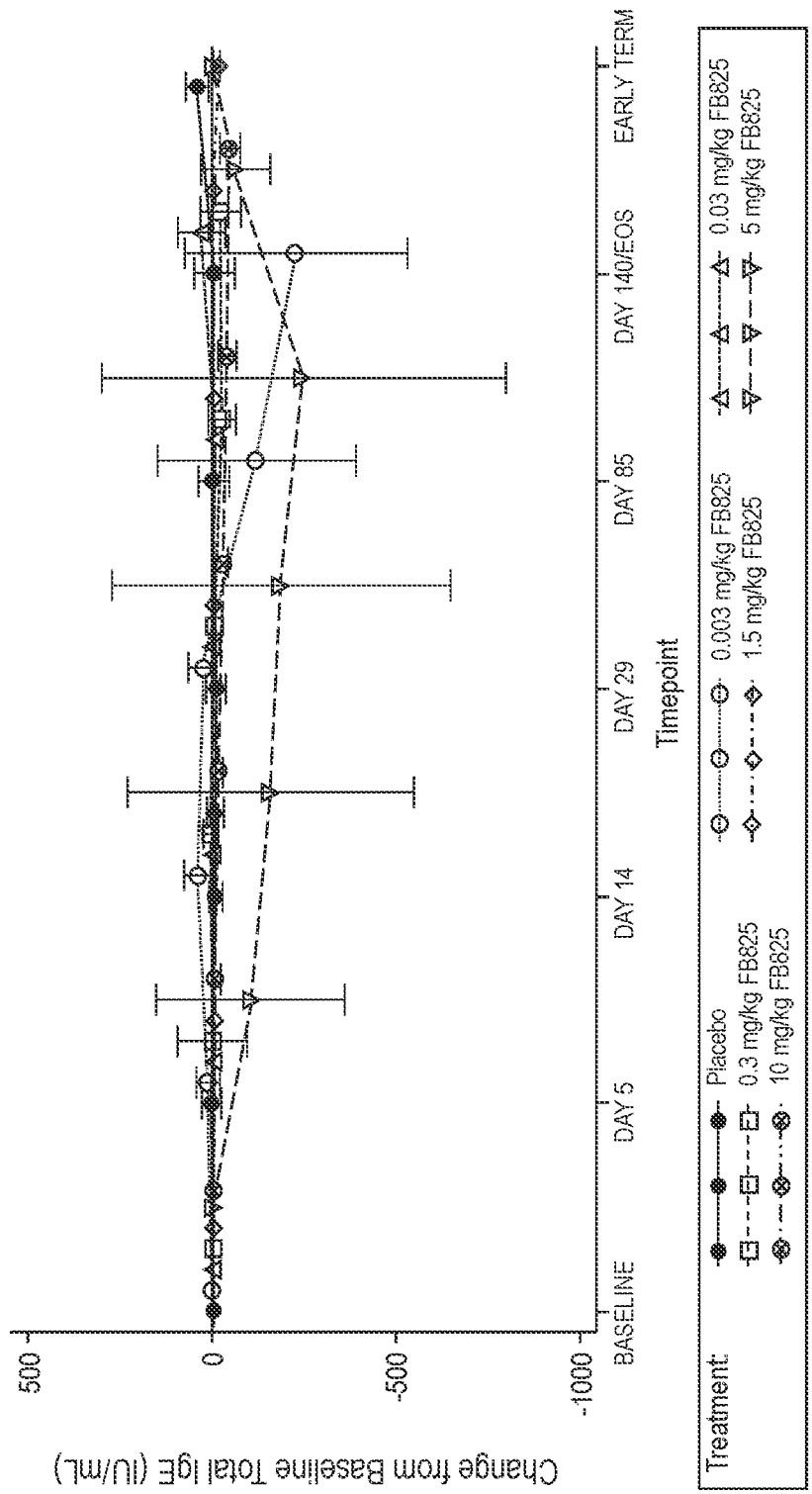
FIG. 1 is a diagram showing the mean (±SD) change from baseline in total IgE over time in human subjects treated by a single dose of FB825. Total IgE was determined from blood samples. Baseline was defined as the last non-missing assessment (including repeated and unscheduled assessments) before study drug administration.

In atopic individuals who are at increased risk of developing allergies, the IgE concentration in the circulatory system may reach over 10 times the normal level. The concentration of allergen-specific IgE antibody is closely correlated with clinical symptoms and may be over 1000 times higher in patients with allergic diseases than in healthy individuals. Immunoglobulin E sensitizes effector cells such as basophils, mast cells, and activated eosinophils by occupying the high-affinity IgE receptor, FcεRI, on which they are expressed. In type I hypersensitivity, allergens cross-link IgE molecules bound by FcεRI and subsequently trigger the degranulation of effector cells, releasing proinflammatory mediators, such as histamines and leukotrienes. The IgE-mediated allergic pathway, which generates mediator-related allergic symptoms, initiates immune activities locally or systemically. Basophils and mast cells also release a wide spectrum of inflammatory cytokines and chemokines that not only cause clinical symptoms directly but also activate and recruit various cell types to augment inflammatory status. Hence, anti-IgE therapy can attenuate both the IgE-mediated pathway and inflammatory conditions.

Described herein are anti-CεmX antibodies for use in reducing the total IgE level and thus treating Ig-E medicated disorders. Such antibodies can be administered to a subject in need of the treatment by at least two doses, which can be at least 8 weeks (e.g., 10 weeks, 12 weeks or 3 months) apart.

Antibodies Capable of Binding to a CεmX Domain of a Membrane-Bound IgE

CεmX is a 52-amino acid segment located between the CH4 domain and the C-terminal membrane-anchoring segment of human membrane-bound ε chain (mε). The amino acid sequence of an exemplary CεmX fragment of human mIgE is provided below (SEQ ID NO:6):

```
GLAGGSAQSQ RAPDRVLCHS GQQQGLPRAA GGSVPHPRCH
CGAGRADWPG PP
```

The antibodies described herein can bind to the CεmX domain of a mIgE, for example, mIgE expressed on the surface of B cells. Such antibodies may induce cell death of the B cells expressing mIgE via, for example, antibody-dependent cell cytotoxicity and/or cell apoptosis, thereby eliminate the B cells, which would lead to reduced production of free IgE. Accordingly, the anti-CεmX antibodies described herein can reduce the level of total IgE in a subject (e.g., a human patient) being treated with the antibody.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used in the methods described herein can be murine, rat, human, or any other origin (including chimeric or humanized antibodies).

Any of the antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In one example, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some examples, the antibody disclosed herein specifically binds a Cεmx domain of a membrane-bound IgE, which may be expressed on the surface of a B cell. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to a CεmX domain epitope is an antibody that binds this CεmX domain epitope with greater affinity, avidity, more readily, and/or with greater duration than it binds to other CεmX domain epitopes or non-CεmX domain epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

The binding affinity of an anti-CεmX antibody described herein can be less than about 100 nM, e.g., less than about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$. One way of determining binding affinity of antibodies to CεmX is by measuring binding affinity of monofunctional Fab fragments of the antibody. To obtain monofunctional Fab fragments, an antibody (for example, IgG) can be cleaved with papain or expressed recombinantly. The affinity of an anti-CεmX Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as koff/kon.

In some embodiments, the antibody binds the CεmX domain of a human IgE, and does not significantly bind an IgE from another mammalian species. In some embodiments, the antibody binds human IgE as well as one or more IgE from another mammalian species. The epitope(s) bound by the antibody can be continuous or discontinuous.

In some embodiments, the anti-CεmX antibody described herein binds an N-terminal portion of the CεmX domain, e.g., GLAGGSAQSQRAPDRVL (SEQ ID NO:1) or GLAGGSAQSQRA (SEQ ID NO:7). Such an antibody may have the same heavy chain and/or light chain CDRs as antibody 4B12/FB825 as described in FIG. 4. See also U.S. Pat. No. 8,460,664, the relevant disclosures therein are incorporated by reference herein. The anti-CεmX antibody may be a humanized antibody of 4B12 (e.g., FB825). In some examples, the anti-CεmX antibody for use in the methods described herein is FB825, which is a humanized antibody of 4B12 (FIG. 4), or a functional variant thereof. See also U.S. Pat. No. 8,460,664, the relevant disclosures therein are incorporated by reference herein.

Two antibodies having the same $V_H$ and/or $V_L$ CDRs means that their CDRs are identical when determined by the same approach (e.g., the Kabat approach, the Chothia approach, the AbM approach, the Contact approach, or the IMGT approach as known in the art. See, e.g., bioinf.org.uk/abs/).

A functional variant (equivalent) of FB825 has essentially the same epitope-binding specificity as FB825 and exhibits substantially similar bioactivity as FB825, including the activity of eliminating B cells expressing mIgE and reducing the level of total IgE in a subject. In some embodiments, a functional variant of FB825 contains the same regions/residues responsible for antigen-binding as FB825, such as the same specificity-determining residues in the CDRs or the whole CDRs. In other embodiments, a functional variant of FB825 comprises a $V_H$ chain that includes a $V_H$ CDR1, $V_H$ CDR2, and $V_H$ CDR3 at least 75% (e.g., 80%, 85%, 90%, 95%, or 98%) identical to the corresponding $V_H$ CDRs of FB825, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of FB825. For example, a functional variant of FB825 may comprise a $V_H$ chain that includes up to 5 (e.g., 1, 2, 3, 4, or 5) amino acid residue variations in the $V_H$ CDR regions ($V_H$ CDR1, CDR2, and/or CDR3 in total) as compared to the $V_H$ CDRs of mAb7E, and/or a $V_L$ chain that includes up to 5 (e.g., 1, 2, 3, 4, or 5) amino acid residue variations in the $V_L$ CDR regions ($V_L$ CDR1, CDR2, and/or CDR3 in total) as compared to the $V_H$ CDRs of mAb7E.

Alternatively, the functional variant of FB825 comprises a $V_H$ chain at least 75% (e.g., 80%, 85%, 90%, 95%, or 98%) identical to the $V_H$ chain of FB825 and a $V_L$ chain at least 75% (e.g., 80%, 85%, 90%, 95%, or 98%) identical to the $V_L$ chain of FB825. The amino acid sequence variations may occur only in one or more of the $V_H$ and/or $V_L$ framework regions.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, the anti-CεmX antibody for use in the treatment method disclosed herein may have one of the following heavy chain variable regions (CDRs following the Kabat definition are in boldface and underlined):

```
                                           (SEQ ID NO: 2)
QVQLQESGPGLVKPSETLSLTCTVSGYSITSDYAWNWIRQPPGKGLEWIG

SISYSGITGYNPSLKSRVTISVDTSKNQFSLKLSSVTAADTAVYYCARMG

YDGLAYWGQGTLVTVSS (SEQ ID NO: 8)
QVQLQESGPGLVKPSETLSLTCTVSGYSITSDYAWNWIRQPPGKGLEWMI

SISYSGITGYNPSLKSRVTISVDTSKNQFSLKLSSVTAADTAVYYCARMG

YDGLAYWGQGTLVTVSS (SEQ ID NO: 9)
QVQLQESGPGLVKPSETLSLTCTVSGYSITSDYAWNWIRQPPGKGLEWIG

SISYSGITGYNPSLKSRVTISRDTSKNQFSLKLSSVTAADTAVYYCARMG

YDGLAYWGQGTLVTVSS
```

Alternatively or in addition, the anti-CεmX antibody for use in the treatment method disclosed herein may have one of the following light chain variable regions (CDRs following the Kabat definition are in boldface and underlined):

```
                                           (SEQ ID NO: 3)
DIVMTQTPLSLSVTPGQPASISCRSSQSIVHSNGNTYLEWYLQKPGQSPQ

LLIYKVSNRFSGVPDRFSGSGSGTEFTLKISRVEAEDVGVYYCFQGSHVP

PTFGGGTKVEIKR (SEQ ID NO: 10)
DIVMTQTPLSLSVTPGQPASISCRSSQSIVHSNGNTYLEWYLQKPGQSPQ

LLIYKVSNRFSGVPDRFSGSGSGTDFTLKISRVEAEDVGVYYCFQGSHVP

PTFGGGTKVEIKR
```

Antibody Preparation

Antibodies capable of binding a CεmX domain of a membrane-bound IgE as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., a CεmX domain of a mIgE such as a human mIgE) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-CεmX monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of binding the CεmX domain. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N═C═NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in reducing total IgE. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to IgE can be identified from the library following routine procedures.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the IgE polypeptide have been replaced (swapped) with sequences from a closely related, but antigenically distinct protein (such as another member of the immunoglobulin protein family). By assessing binding of the antibody to the mutant immunoglobulin, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Pharmaceutical Compositions

One or more of the above-described anti-CεmX antibodies can be mixed with a pharmaceutically acceptable carrier (excipient), including buffer, to form a pharmaceutical composition for use in treating a disorder associated with IgE. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. In one example, a pharmaceutical composition contains more than one anti-CεmX antibodies that recognize different epitopes of the target antigen.

The pharmaceutical compositions to be used in the present methods can comprise pharmaceutically acceptable carriers, excipients, or stabilizers in the form of lyophilized formulations or aqueous solutions. Remington: The Science and Practice of Pharmacy 20th Ed. (2000) Lippincott Williams and Wilkins, Ed. K. E. Hoover. Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the anti-CεmX antibody, which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-CεmX antibody may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(v nyl-alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In some embodiments, the pharmaceutical composition comprising the anti-CεmX antibody described herein, e.g., FB825 or a functional variant thereof as also described herein, may be an aqueous formulation, which may further comprise a buffer (which may comprise an amino acid such as histidine or arginine), a salt (e.g., sodium chloride), and/or a surfactant, such as a nonionic surfactant. For example, the aqueous formulation may comprise the antibody at a concentration of about 10-30 mg/ml, a buffer comprising an amino acid (e.g., histidine or arginine) at a concentration of about 10-30 mM, a surfactant such as polysorbate 80 at a concentration of about 0.01-0.03%, and/or a sodium chloride at a concentration of about 120-160 mM. Such an aqueous formulation may have a pH of about 5-8. In one particular example, the aqueous formulation may comprise antibody FB825 at a concentration of about 20 mg/ml, L-histidine at a concentration of about 20 mM, sodium chloride at a concentration of about 140 mM, polysorbate 80 at a concentration of about 0.02%, and a pH of about 6.5.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an anti-CεmX antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Use of Anti-CεmX Antibodies for Treating Disorders Associated with IgE

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-CεmX antibodies can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a disorder associated with IgE (e.g., allergic asthma, as well as other disorders known in the art and/or disclosed herein). A subject having an IgE-associated disorder such as allergic asthma can be identified by routine medical examination, e.g., laboratory tests. A subject suspected of having the IgE-associated disorder might show one or more symptoms of the disorder, e.g., elevated levels of IgE and/or hyperreactivity to an allergen and/or antigen. A subject at risk for the disorder can be a subject having one or more of the risk factors for that disorder.

Exemplary IgE-associated disorders include, but are not limited to, asthma, allergic rhinitis, hyper IgE syndrome, atopic dermatitis, cold-induced urticaria, chronic urticaria, cholinergic urticaria, chronic rhinosinusitis, systemic mastocytosis, cutaneous mastocytosis, allergic bronchopulmonary aspergillosis, recurrent idiopathic angioedema, and interstitial cystitis, eosinophil-associated gastrointestinal disorders, a food allergy, or a drug allergy.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a disorder associated with IgE. Alternatively, sustained continuous release formulations of an anti-CεmX antibody may be appropriate. Various formulations and devices for achieving sustained release are known in the art.

In one example, dosages for an anti-CεmX antibody as described herein may be determined empirically in individuals who have been given one or more administration(s) of an anti-CεmX antibody. Individuals are given incremental dosages of the anti-CεmX antibody. To assess efficacy of the anti-CεmX antibody, an indicator of a disorder associated with IgE (such as levels of IgE) can be followed.

For the purpose of the present disclosure, the appropriate dosage of an anti-CεmX antibody will depend on the specific anti-CεmX antibody(s) (or compositions thereof) employed, the type and severity of disorder associated with IgE, whether the antibody is administered for preventive or therapeutic purposes, previous therapy, the patient's clinical history and response to the antibody, and the discretion of the attending physician. Typically the clinician will administer an anti-CεmX antibody, such as FB825, until a dosage is reached that achieves the desired result. Administration of an anti-CεmX antibody can be continuous or intermittent, depending, for example, upon the recipient's physiological condition, whether the purpose of the administration is therapeutic or prophylactic, and other factors known to skilled practitioners.

In some embodiments, the anti-CεmX antibody (e.g., FB825) described herein is administered to a subject in need of the treatment at an amount sufficient to reduce the level of the total IgE level by at least 20% (e.g., 30%, 40%, 50%, 60%, 70%, 80%, 90% or greater).

As used herein, the term "treating" refers to the application or administration of a composition including one or more active agents to a subject, who has a disease associated with IgE, a symptom of a disease associated with IgE, or a predisposition toward the disease, with the purpose to cure, heal, alleviate, relieve, alter, remedy, ameliorate, improve, or affect the disorder, the symptom of the disease, or the predisposition toward the disease.

Alleviating a disease associated with IgE includes delaying the development or progression of the disease, or reducing disease severity. Alleviating the disease does not necessarily require curative results. As used therein, "delaying" the development of a disease (such as a disease associated with IgE) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease associated with IgE includes initial onset and/or recurrence.

To perform the methods as described herein, any of the anti-Cεmx antibodies such as FB825 may be given to a subject in need of the treatment (e.g., a human patient) by a single dose or by multiple doses via a suitable route, for example, intravenous infusion or subcutaneous injection. The dosage of the anti-Cεmx antibody for each administration may range from about 0.5 mg/kg to about 25 mg/kg (e.g., about 1 mg/kg to about 20 mg/kg, about 5 mg/kg to about 15 mg/kg, or about 10 mg/kg to about 20 mg/kg), depending upon various factors, including those described herein. For repeated administrations over several days or longer, depending on the condition, the treatment is sustained until a desired suppression of symptoms occurs or until sufficient therapeutic levels are achieved to alleviate a disorder associated with IgE, or a symptom thereof.

The administration of an anti-CεmX antibody (e.g., FB825) may be essentially continuous over a preselected period of time or may be in a series of spaced dose, e.g., either before, during, or after developing a disorder associated with IgE. An exemplary dosing regimen comprises administering to a subject in need of the treatment a first dose of an anti-Cεmx antibody (e.g., at 3 mg/kg, 5 mg/kg, 10 mg/kg, 15 mg/kg, 20 mg/kg, or 25 mg/kg), followed by a second dose of the antibody at least 3 months after the first dose (e.g., 4 months, 5 months, or 6 months). The dosage of the second administration may be higher, the same, or lower than the first administration. Other dosage regimens may be useful depending upon the pattern of pharmacokinetic decay that a practitioner wishes to achieve.

In some embodiments, a subject in need of the treatment can be given a first dose of the antibody at a suitable amount (e.g., at 3 mg/kg, 5 mg/kg, 10 mg/kg, 15 mg/kg, 20 mg/kg, or 25 mg/kg). The subject is then monitored periodically for symptoms indicative of an IgE-associated disorder, for example, allergic reactions and/or an elevated level of total IgE. A second dose of the antibody may be given to the subject when such a symptom is observed.

Also within the scope of the present disclosure are preventive treatments of an IgE-associated disorder with any of the anti-Cεmx antibodies to reduce the risk for occurrence of such a disorder. Subjects suitable for such a preventive treatment may be human patients having history of an IgE-associated disorder and/or family history of an IgE-associated disorder.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an anti-CεmX antibody is administered via site-specific or targeted local delivery techniques. Examples of site-specific or targeted local delivery techniques include various implantable depot sources of the anti-CεmX antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568. Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed. Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

It is also apparent that an expression vector can be used to direct expression of any of the protein-based anti-CɛmX antibodies described herein (e.g., FB825). For example, other anti-CɛmX antibody fragments that are capable of binding CɛmX and/or an IgE biological activity are known in the art.

The particular dosage regimen, i.e., dose, timing and repetition, used in the method described herein will depend on the particular subject and that subject's medical history. Any of the anti-Cmex antibodies described herein may be used in conjunction with other agents (e.g., other agents for treating IgE-associated disorders) that serve to enhance and/or complement the effectiveness of the agents.

In some embodiments, an anti-CɛmX antibody as described herein, for example, FB825, is used for treating atopic dermatitis as follows. Atopic dermatitis, also known as eczema, is a chronical skin condition characterized by redness and/or itchy. It is common in children but can occur at any age. A patient who needs the treatment can be identified by routine medical practice as having one or more symptoms of atopic dermatitis, including dry skin, itching, red to brownish-gray patches, small, raised bumps, which may leak fluid and crust over when scratched, thickened, cracked, scaly skin, and/or raw, sensitive, swollen skin from scratching. In some instances, the total IgE level and the level of allergen-specific IgE of a candidate subject can be examined via routine practice. If the IgE level of the candidate subject (e.g., the total IgE, the allergen-specific IgE, or both) is higher than a normal level (representing the average IgE level in subjects of the same species, e.g., humans, who are free of atopic dermatitis or other allergic disorders associated with IgE).

A human patient who needs the treatment may be given a first dose of the antibody, which may range from 3 mg/kg to 8 mg/kg, via a conventional route as described herein. In some instances, the first dose is 5 mg/kg. After the first dose, the total IgE level of the patient can be monitored. If the reduction of the IgE level 3-4 weeks after the first dose is less than 50%, a second dose of the antibody may be given to the patient 3-4 weeks after the first dose. The second dose may be identical to the first dose, or lower than the first dose. In some instances, both the first dose and the second dose are 5 mg/kg and are administered via IV infusion in a 1-2 hour period. Other biomarkers indicating efficacy and/or safety could also be monitored during the course of the treatment. Such biomarkers include, but are not limited to, thymus and activation regulated chemokine (TARC), Eotaxin-3, thymic stromal lymphopoietin (TSLP), periostin, IL-1a, IL-4, IL-5, IL-13, IL-16, IL-31, M-CSF, or a combination thereof.

The human patient subject to the above-noted treatment may have chronic atopic dermatitis for at least 3 years as diagnosed by routine medical practice, for example, defined by the Eishenfield revised criteria of Hannifin and Rajka and supported by positive allergen-specific IgE. The patient may have one or more of the following features: (i) eczema area and severity index (EASI) score greater than 14, (ii) Investigator's Global Assessment (IGA) score greater than 3 (5-point scale), (iii) greater than 10% body surface area (BSA), (iv) history of inadequate response to a stable regimen of topical corticosteroids or calcineurin inhibitors for at least one month or at least three months before the treatment. Further, the human patient may be given stable doses of emollient twice daily for at least 7 days before the treatment.

In some instances, the anti-CɛmX antibody as described herein (e.g., FB825) may be co-used with moisturizers (e.g., at stable doses such as at least twice daily) and/or topical corticosteroid (TCS). A medium potency TCS may be applied to areas with active lesions and may switch to low potency TCS after the lesions are under control. If lesions reoccur, treatment with a medium potency TCS may resume with a step-down approach. If lesions are persisting or worsening after daily treatment with a medium potency TCS, a high or super-high potency TCS may be used, unless it is deemed unsafe. A low potency TCS may be used on areas of thin skin (e.g., face, neck, intertriginous, genital areas, or areas of skin atrophy) or on areas where continued use of medium potency TCS is considered unsafe.

TCS having low, medium, and high or super-high potency is well known in the art. Exemplary medium potency TCS includes 0.05% fluticasone propionate cream, 0.1% mometasone furoate cream, or 0.06% betamethasone valerate cream. Exemplary low potency TCS includes 1% hydrocortisone ointment. Exemplary high potency TCS can be 0.05% fluocinonide cream or 0.25% desomimetasone ointment. Exemplary super-high potency TCS can be 0.05% clobetasol propionate ointment.

In some instances, the patient subject to the treatment described herein is free of one or more of the following therapy: (i) topical tacrolimus and pimecrolimus, (ii) systemic treatment of corticosteroids, (iii) leukotriene inhibitors, (iv) allergen immunotherapy, (v) systemic treatment of immunosuppressors or immunomodulators (e.g., cyclosporine, mycophenolate-mofetil, azathioprine, methotrexate, or biologics), (vi) live (e.g., attenuated) vaccines, and/or (vii) traditional Chinese medicine. The patient may also be free of any surgical procedures and/or UV procedures.

Any of the methods described herein may further comprise assessing occurrence of decreased hemoglobin, upper respiratory tract infection, urinary tract infection, or a combination thereof in the subject after the first dose. If one or more occurrences are observed, the amount of the anti-Cεmx antibody (e.g., FB825) of the second dose may be reduced. Alternatively, the treatment may be stopped.

Kits for Use in Treating IgE-Associated Disorders

The present disclosure also provides kits for use in treating IgE-associated disorders. Such kits can include one or more containers comprising an anti-Cεmx antibody as described herein (such as FB825).

In some embodiments, the kit can comprise instructions for use in accordance with any of the methods described herein. The included instructions can comprise a description of administration of the anti-Cεmx antibody to treat, delay the onset, or alleviate an IgE-associated disorder according to any of the methods described herein. The kit may further comprise a description of selecting an individual suitable for treatment based on identifying whether that individual has, is suspected of having, or is at risk for the disorder. In still other embodiments, the instructions comprise a description of administering anti-Cεmx antibody to a subject in need of the treatment to reduce the risk for developing the IgE-associated disorder.

The instructions relating to the use of an anti-Cεmx antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating an IgE-associated disorder. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-Cεmx antibody, such as FB825.

Kits may optionally provide additional components such as buffers and interpretive information. Normally, the kit comprises a container and a label or package insert(s) on or associated with the container. In some embodiments, the present disclosure provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Toxicity Studies of FB825 in Cynomolgus Monkey

Materials and Methods

Laboratory Tests

Blood and urine samples for hematology, coagulation, serum chemistry (including liver function tests), thyroid function tests, and urinalysis were collected and analyzed following routine clinical laboratory tests.

Abnormal clinical laboratory values were flagged as either high or low (or normal or abnormal) based on the reference ranges for each laboratory parameter. Clinical significance was defined as any variation in results that had medical relevance and may have resulted in an alteration in medical care (e.g., active observation, diagnostic measures, or therapeutic measures). If a clinically significant change from screening was noted, the clinically significant value and reason for clinical significance were documented. The cynomolgus monkey being treated was continued to be monitored with additional assessments until the values reached the reference range or the values at screening or until follow-up was no longer medically necessary.

Pharmacodynamic Assessments

Blood samples for the determination of total IgE and antidrug antibodies (ADA) were collected using 3.5-mL blood collection tubes (BD Vacutainer® SST™ Serum Separation Tubes), provided by Vince and Associates Clinical Research. One sample was collected to target a minimum blood volume per blood collection tube size. A minimum of 1.0 mL of serum was collected at each time point. After obtaining the blood sample, the collection tube was inverted 5 times and the blood was allowed to clot for 30 minutes at ambient temperature (19° C.-24° C.). The sample was centrifuged at approximately 2200 rpm for 10 minutes at room temperature in a swinging bucket centrifuge. Duplicate serum aliquots of approximately equal volume (minimum of 500 μL per aliquot) were transferred, using the standard laboratory technique, into 2 appropriately labeled storage tubes (2-mL polypropylene cryovials) provided by Vince and Associates Clinical Research.

Immunogenicity samples for the measurement of ADA were analyzed using a validated ELISA.

Serum Aspartate Aminotransferase and Alanine Amino Transferase

The liver function in FB825 treated cynomolgus monkeys was monitored by measuring the levels of aspartate aminotransferase (AST) and alanine amino transferase (ALT). The activities of these two enzymes were expressed as unit per liter (U/L).

Results

Single-Dose Studies of FB825 in Cynomolgus Monkeys

Single-dose toxicity of FB825 was assessed in non-GLP single-dose toxicity studies carried out in cynomolgus monkeys. In the first study, treatment-related effects were determined in cynomolgus monkeys administered a single 10-minute IV infusion of FB825. In the second study, treatment-related effects were determined in cynomolgus monkeys administered a single subcutaneous injection of FB825.

In an IV injection dose-range-finding study, a single 10-minute IV infusion of FB825 was well tolerated in male and female cynomolgus monkeys at 30, 100, and 300 mg/kg. There were no treatment-related effects on clinical parameters, food consumption, body weight, or mortality. FB825-related effects were limited to minimal increases in ALT and AST that had recovered by Day 57 and minimal increases in interleukin-6 and interleukin-10 at 6 hours and/or 1 hour after dosing in animals administered at least 100 mg/kg FB825. Based on these results, the no observed adverse effect level (NOAEL) was considered to be 300 mg/kg.

In another single-dose toxicology study, administration of FB825 via a single subcutaneous injection was well tolerated in cynomolgus monkeys at 300 mg/kg. No FB825-related clinical signs or effects on body weights or clinical pathology parameters (hematology, coagulation, and clinical chemistry) were observed.

Repeat-Dose Studies of FB825 in Cynomolgus Monkeys

Repeat-dose toxicity of FB825 was assessed in cynomolgus monkeys. Treatment-related effects were determined in cynomolgus monkeys administered a single 10-minute IV infusion of FB825 once weekly for a total of 4 doses.

Administration of FB825 by 10 minute IV infusion once weekly for a total of 4 doses was well tolerated in cynomolgus monkeys at 30, 100, and 300 mg/kg. The following parameters and end points were evaluated in this study: clinical signs, body weight, food consumption, ophthalmology, electrocardiology, clinical pathology parameters (hematology, coagulation, and clinical chemistry), bioanalysis and toxicokinetic evaluations, antitherapeutic antibody analysis, flow cytometry, IgE analysis, thyroid hormone levels, gross necropsy findings, organ weights, and histopathologic examinations.

No FB825-related clinical signs or effects observed on body weight, food consumption, the ophthalmic and electrocardiographic examinations, coagulation parameters, and thyroid hormone levels were observed in either sex at doses up to 300 mg/kg. Additionally, there were no FB825-related notable gross findings at doses up to and including 300 mg/kg.

FB825-related effects were limited to reversible marked increases in ALT at FB825 doses of higher than or equal to 100 mg/kg, and reversible mild increases in AST, partially reversible minimal decreases in albumin levels and the corresponding albumin:globulin ratios, and reversible minimal increases in monocyte counts at an FB825 dose of 300 mg/kg. The magnitude of the increases in ALT and AST levels at 300 mg/kg were considered adverse. Target organ effects were observed at levels of ≥30 mg/kg and consisted of nonadverse follicular colloid depletion of the thyroid and lower thyroid weight. However, the lower thyroid weights were within the range observed in historical control monkeys. Because variation in colloid staining pattern, variation in thyroid follicle size, and vacuolar degeneration have been reported as spontaneous findings in cynomolgus monkeys (Ishida 2000; Hatakeyama 2011) and because there were no test article-related effects on thyroxine and thyroid-stimulating hormone levels, the findings in the thyroid were considered nonadverse under the conditions of this study.

Based on the increases in ALT and AST levels at 300 mg/kg, the NOAEL was considered to be 100 mg/kg ($C_{max}$ of 5330 μg/mL and $AUC_{(0\text{-}168\ h)}$ of 520 mg·hr/mL for males and $C_{max}$ of 5220 μg/mL and $AUC_{(0\text{-}168\ h)}$ of 487 mg·hr/mL for females).

Example 2: Human Clinical Studies

The primary objective of this study was to evaluate the safety and tolerability of single ascending IV doses of FB825 in normal, healthy subjects. The secondary objectives of this study include determination the PK profile of single ascending IV doses of FB825, to explore the effects on total IgE after single ascending IV doses of FB825, and to explore the occurrence of anti-FB825 antibodies after single ascending IV doses of FB825.

Study Design

This was a Phase 1, first-in-human (FIH), randomized, double-blind, placebo-controlled study to evaluate the safety, tolerability, pharmacokinetics, and immunogenicity of single ascending IV doses of FB825. An overview of the schedule of events performed during the FB825 human clinical study is described in Table 1. Subjects who met the criteria for study entry were assigned to the current dose cohort and randomly assigned to receive FB825 or placebo (vehicle). All doses of FB825 were administered as a 1-hour IV infusion.

The safety data for each dose cohort were reviewed before progression to the next-highest-dose cohort. Dosing for the next-highest-dose cohort was permitted only after confirmation of the safety to do so. A dose level could have been adjusted, or repeated, as necessary. Blinded PK data was reviewed at the same time as the blinded safety data.

The study included 6 cohorts and a total of approximately 54 normal, healthy subjects (7 subjects each [4 active: 3 placebo] in Cohorts A and B and 10 subjects each [7 active: 3 placebo] in Cohorts C, D, E, and F). The starting FB825 dose was 0.003 mg/kg IV with planned increases in subsequent cohorts to 0.03, 0.3, 1.5, 5, and 10 mg/kg IV. The study consisted of a screening period (Days −28 to −2), check-in (Day −1), a treatment/follow-up period (Days 1 to 140), and an end-of-study visit (Day 140).

Subjects checked into the clinic on Day −1, and check-in procedures were performed. When procedures overlapped and were scheduled to occur at the same time point, the order of procedures was vital sign measurements, electrocardiograms, and then pharmacokinetic blood collection.

Subjects received active or placebo study drug on Day 1. The first 2 subjects from the 2 lowest-dose cohorts (Cohorts A and B) received either placebo or FB825 (i.e., both placebo and active study drug were required to be represented). The remaining subjects in these cohorts were dosed 48 hours after the first 2 subjects were dosed. All subjects in the 4 highest-dose cohorts were dosed at the same time. There was a minimum of 14 days between the dosing of the last subject in a cohort before a decision was made to proceed with dosing the next cohort. Safety data for each dose cohort were reviewed in a blinded fashion before progression to the next-highest-dose cohort. Dosing in the next-highest-dose cohort was permitted only after confirmation that it was safe to do so. Blinded PK data was reviewed at the same time as the blinded safety data.

Blood samples for PK assessments were collected on Day 1 at 30 minutes (±5 minutes) before the start of infusion; at 30 minutes (±2 minutes) after the start of infusion; at 1, 1.25, and 2 hours (±2 minutes) after the start of infusion; at 4 and 8 hours (±5 minutes) after the start of infusion; and at 24 and 48 hours (±10 minutes) after the start of infusion. In addition, single blood samples were collected on Days 5, 14, 29, 85, and 140 after infusion. Blood samples for immunogenicity assessments were collected on Day 1 (30 minutes [±5 minutes] before the start of infusion) and on Days 5, 14, 29, 85, and 140.

Subjects were confined within the clinic from Day −1 until discharge on Day 3 (48 hours after dosing) and returned to the clinic on Days 5, 14, 29, 85, and 140 for outpatient visits. The duration of the study, excluding screening, was approximately 140 days.

Patient Population

Healthy male and female subjects, 18 to 55 years of age, inclusive, had a body weight higher than or equal to 50 kg and a body mass index of 18.0 to 30.0 kg/m2, inclusive, and provided written informed consent. A total of 54 subjects were enrolled, 41 subjects (75.9%) completed the study, and 13 subjects (24.1%) were discontinued. Seven subjects (13.0%) discontinued due to subject choice and included 1 subject each in the 0.3, 1.5, 5, and 10 mg/kg FB825 treatment groups and 3 subjects in the placebo treatment group. Six subjects (11.1%) were lost to follow-up and included 1 subject each in the 0.003, 0.3, and 1.5 mg/kg FB825 and placebo treatment groups and 2 subjects in the 10 mg/kg FB825 treatment group.

TABLE 1

Schedule of Events.

| | | | | Procedure | | | | | | |
|---|---|---|---|---|---|---|---|---|---|---|
| | | | | Confinement | | | | Outpatient Visits | | |
| | | | | 2 | 3 | | | | | |
| Study Day(s) | Screening −28 to −2 | Check-in −1 | 1 | (24 h after dosing) | (48 h after dosing) | 5 | 14 (+/−1 day) | 29 (+/−1 day) | 85 (+/−1 day) | 140 (EOS) (+/−1 day) |
| Informed consent | X | | | | | | | | | |
| Inclusion/Exclusion criteria | X | X | | | | | | | | |
| Medical history | X | X | | | | | | | | |
| Physical examination | X | X | | | X | X | X | X | X | X |
| Vital sign measurements | X | X | X | X | X | X | X | X | X | X |
| 12-Lead ECG | X | X | X | X | X | X | X | | | X |
| Cardiac telemetry | | | X | | | | | | | |
| Serology | X | | | | | | | | | |
| Clinical laboratory testing | X | X | X | X | X | X | X | X | X | X |
| Thyroid function testing | X | X | | | | | X | X | X | X |
| Urine, drug, cotinine, and alcohol screen | X | X | | | | | | | | |
| Serum pregnancy test (female subjects) | X | X | | | X | | | | | X |
| Serum FSH | X | | | | | | | | | |
| Admission to clinic | | X | | | | | | | | |
| Randomization | | | X | | | | | | | |
| Study drug administration | | | X | | | | | | | |
| Pharmacokinetic blood sampling | | | X | X | X | X | X | X | X | X |

TABLE 1-continued

Schedule of Events.

| | | | | Procedure | | | | | | |
|---|---|---|---|---|---|---|---|---|---|---|
| | | | | Confinement | | | | | | |
| | | | | 2 | 3 | | Outpatient Visits | | | |
| Study Day(s) | Screening −28 to −2 | Check-in −1 | 1 | (24 h after dosing) | (48 h after dosing) | 5 | 14 (+/−1 day) | 29 (+/−1 day) | 85 (+/−1 day) | 140 (EOS) (+/−1 day) |
| Total IgE and ADA sampling | | | | X | | X | X | X | X | X |
| Adverse events assessment | | X | X | X | X | X | X | X | X | X |
| Prior and concomitant medications | X | X | X | X | X | X | X | X | X | X |
| Discharge from clinic | | | | | X | | | | | |
| Study discharge | | | | | | | | | | X |

Abbreviations: ADA, antidrug antibodies;
ECG, electrocardiogram;
EOS, endofstudy;
FSH, follicle-stimulating hormone;
Ig, immunoglobulin.

FB825 Administration

On Day 1, subjects received a single IV infusion of FB825 (0.003, 0.03, 0.3, 1.5, 5, or 10 mg/kg) or placebo over approximately 1 hour.

All doses were administered in the morning of the scheduled dosing day (Day 1) as a single, approximately 1-hour IV infusion after a fast of approximately 2 hours. A light breakfast was permitted 2 hours or more before dosing. Water was permitted at any time except for 1 hour before and 1 hour after dosing. The FB825 solutions were diluted before administration.

A single, approximately 1-hour intravenous infusion of FB825 or placebo was administered on Day 1 at 0 hours. Progress to the next dose level was dependent on Safety Review Team approval. The first 2 subjects from the 2 lowest-dose cohorts (Cohorts A and B) received either placebo or FB825 (i.e., both placebo and active were required to be represented). The remaining subjects in these cohorts were dosed 48 hours after the first 2 subjects had been dosed. All subjects in the 4 highest-dose cohorts were dosed at the same time.

Pharmacokinetic (PK) Assessments

Blood samples for PK analysis of FB825 were collected from all subjects at the following time points: on Day 1 at 30 minutes (±5 minutes) before the start of infusion; at 30 minutes (±2 minutes) after the start of infusion; at 1, 1.25, and 2 hours (±2 minutes for 30 minutes to 2 hours postdose) after the start of infusion; at 4 and 8 hours (±5 minutes for 4 to 8 hours postdose) after the start of infusion; and at 24 and 48 hours (±10 minutes for 24 to 48 hours postdose) after the start of infusion. In addition, single blood samples were collected on Days 5, 14 (±1 day), 29 (±2 days), 85 (±3 days), and 140 (±5 days) after infusion.

The following single-dose PK parameters were calculated for FB825 from the serum concentration data for each subject using noncompartmental methods:

$AUC_{0-t}$ Area under the serum concentration-time curve (AUC) from time 0 to the last quantifiable concentration, calculated using the linear trapezoidal rule $AUC_{0-inf}$ AUC from time 0 extrapolated to infinity, calculated using the following formula:

$$AUC_{0-inf} = AUC_{0-t} + C_t/K_{el},$$

where $C_t$ was the last measurable serum concentration, and $K_{el}$ was the terminal elimination rate constant. If the extrapolated area $(C_t/K_{el})$ was greater than 20% of $AUC_{0-inf}$, then $AUC_{0-inf}$ and its associated parameters (CL and $V_d$) were set to missing.

% $AUC_{ex}$ Percentage of the area extrapolated for calculation of $AUC_{0-inf}$ $C_{max}$ Maximum observed serum concentration $T_{max}$ Time of maximum observed serum concentration $K_{el}$ Terminal elimination rate constant, where $K_{el}$ was the magnitude of the slope of the linear regression of the log concentration versus time profile during the terminal phase. $K_{el}$ was only retained if $R^2 \geq 0.80$ and 3 points in the terminal phase did not include $C_{max}$.

$t_{1/2}$ Terminal half-life (whenever possible), calculated as $(\ln)2/K_{el}$

MRT Mean residence time, calculated as AUMC/AUC

CL Apparent clearance, calculated as $Dose/AUC_{0-inf}$ $V_d$ Apparent volume of distribution, calculated as follows:

$$Dose/(AUC_{0-inf} \times K_{el})$$

Pharmacokinetic Blood Samples

Blood samples to analyze FB825 were collected using 3.5 mL blood collection tubes (BD Vacutainer® SST™ serum separation tubes), provided by Vince and Associates Clinical Research. One sample was collected to target a minimum blood volume per blood collection tube size. A minimum of 1.0 mL of serum was collected at each time point. After obtaining the blood sample, the collection tube was inverted 5 times, and the blood was allowed to clot for 30 minutes at ambient temperature (19° C.-24° C.). The sample was centrifuged at approximately 2200 rpm for 10 minutes at room temperature in a swinging bucket centrifuge. Duplicate serum aliquots of approximately equal volume (minimum of 500 µL per aliquot), using standard laboratory technique, were transferred into 2 appropriately labeled storage tubes (2-mL polypropylene cryovials) provided by Vince and Associates Clinical Research. A label was secured to each storage tube and contained the following information:

Sample Type: Human serum
Assay Type: PK
Protocol: FB825CLCT01

Subject Number: Randomization number
Time point: Refer to protocol
Serum Aliquot: 1 or 2

Within 90 minutes of collection, both aliquot samples were stored upright at −70° C.±10° C. Pharmacokineticserum determinations of FB825 were performed using a validated ELISA.

Pharmacodynamic Assessments

Blood samples for the determination of total IgE and antidrug antibodies (ADA) were collected on Day 1 at 30 minutes (±5 minutes) before the start of infusion and on Days 5, 14 (±1 day), 29 (±2 days), 85 (±3 days), and 140 (±5 days) after the infusion, or at early termination.

Blood samples for analysis of the ADA levels were collected using 3.5-mL blood collection tubes (BD Vacutainer® SST™ Serum Separation Tubes), provided by Vince and Associates Clinical Research. One sample was collected to target a minimum blood volume per blood collection tube size. A minimum of 1.0 mL of serum was collected at each time point. After obtaining the blood sample, the collection tube was inverted 5 times and the blood was allowed to clot for 30 minutes at ambient temperature (19° C.-24° C.). The sample was centrifuged at approximately 2200 rpm for 10 minutes at room temperature in a swinging bucket centrifuge. Duplicate serum aliquots of approximately equal volume (minimum of 500 μL per aliquot) were transferred, using the standard laboratory technique, into 2 appropriately labeled storage tubes (2-mL polypropylene cryovials). Immunogenicity samples for the measurement of ADA were analyzed using a validated ELISA.

Safety Assessments

Safety and tolerability were assessed by monitoring and recording AEs, clinical laboratory test results (hematology, coagulation, serum chemistry including liver function tests, thyroid function tests, and urinalysis), vital sign measurements, 12-lead ECG results, cardiac telemetry data, and physical examination findings.

Clinical Laboratory Tests

Blood and urine samples for hematology, coagulation, serum chemistry (including liver function tests), thyroid function tests, urinalysis, and drug screen tests were collected under fasting conditions (fasted for approximately 2 or more hours) at the time points indicated in the schedule of events (Table 1). Clinical laboratory tests (hematology, coagulation, serum chemistry [including liver function tests], and urinalysis) were performed at screening; checkin; on Day 1 before the start of infusion and at 1 (end of infusion), 8, and 24 hours (±15 minutes) after the start of the infusion; and at a single time point on Days 3 (±15 minutes for up to 48 hours postdose), 5, 14, 29, 85, and 140.

The samples were used for clinical laboratory tests including hematology, coagulation, serum chemistry, thyroid function, and urinalysis.

A serum pregnancy test (β-human chorionic gonadotropin) was performed on all female subjects at screening, check-in, on Day 3 (48 hours after dosing), and at the end-of-study visit (Day 140). Female subjects who were postmenopausal had a serum FSH test at screening.

Hepatitis B surface antigen, hepatitis C virus antibody, and human immunodeficiency virus (types 1 or 2) antibody were assessed at screening.

A urine drug screen was performed at screening and on Day −1 for alcohol, amphetamines, barbiturates, benzodiazepines, cocaine metabolites, cotinine, methylenedioxymethamphetamine, opiates, phencyclidine, propoxyphene, and tetrahydrocannabinol.

Abnormal clinical laboratory values were flagged as either high or low (or normal or abnormal) based on the reference ranges for each laboratory parameter. Clinical significance was defined as any variation in results that had medical relevance and may have resulted in an alteration in medical care (e.g., active observation, diagnostic measures, or therapeutic measures). If a clinically significant change from screening was noted, the clinically significant value and reason for clinical significance were documented on the AE page in the eCRF. The subjects were monitored continuously with additional assessments until the values reached the reference range or the values at screening or until follow-up was no longer medically necessary.

Vital Sign Measurements

Vital sign measurements included systolic and diastolic blood pressures, heart rate, respiratory rate, and oral body temperature. The subject was seated for at least 5 minutes before all measurements were taken, with the exception of orthostatic assessments. At the time points for orthostatic assessments, after taking all measurements with the subjects seated, subjects were supine for 5 minutes before their blood pressure and heart rate were taken; subjects then stood for 1 minute before their blood pressure and heart rate were taken again.

Vital signs were measured at the time points indicated in the schedule of events (Table 1).

Vital sign measurements (systolic and diastolic blood pressures, heart rate, respiratory rate, and oral body temperature) were obtained at screening; check-in; on Day 1 before the start of infusion and at 1 (end of infusion), 2 and 4 hours (±15 minutes), and 8 and 24 hours (±30 minutes) after the start of the infusion; and on Days 3 (±15 minutes for up to 48 hours postdose), 5, 14, 29, 85, and 140. During the infusion, vital sign measurements were obtained every 15 minutes (±5 minutes). Orthostatic assessments were performed at check-in; on Day 1 before the start of infusion and at 2, 4, 8, and 24 hours (±15 minutes) after the start of the infusion; and on Day 5.

Clinical significance was defined as any variation in results that had medical relevance and may have resulted in an alteration in medical care (e.g., active observation, diagnostic measures, or therapeutic measures). If a clinically significant change from screening was noted, the clinically significant value and reason for clinical significance was documented on the AE page in the subject's eCRF. The subject can be monitored on a continuing basis with additional assessments until the value reached the reference range or the value at screening or until follow-up was no longer medically necessary.

Twelve-Lead Electrocardiogram

Single 12-lead ECGs were obtained after the subject had been in the supine position for at least 5 minutes at the time points indicated in the schedule of events (Table 1). Twelve-lead electrocardiograms were obtained at screening; checkin; on Day 1 within 2 hours before the start of infusion and at 1 (end of infusion), 8, and 24 hours (±15 minutes) after the start of the infusion; and on Days 3 (±15 minutes for up to 48 hours postdose), 5, 14, and 140.

Electrocardiogram assessments included comments on whether the tracings were normal or abnormal, as well as the rhythm, presence of arrhythmia or conduction defects, morphology, evidence of myocardial infarction, and ST segment, T wave, and U wave abnormalities. In addition, measurements of the following intervals were measured and reported: RR interval, PR interval, QRS width, QT interval, and QTcF.

Clinical significance was defined as any variation in results that had medical relevance and may have resulted in an alteration in medical care (e.g., active observation, diagnostic measures, or therapeutic measures). If a clinically significant change from screening was noted, the clinically significant value and reason for clinical significance were documented on the AE page in the subject's eCRF. The subject was monitored continuously with additional assessments until either the values reached the reference range or the values at screening or until follow up is no longer medically necessary.

Cardiac Telemetry

Cardiac telemetry was performed at the time points indicated in the schedule of events (Table 1). Cardiac telemetry monitoring began on Day 1 (starting approximately 30 minutes before the start of infusion) and continued for 4 hours after the end of the infusion.

Clinical significance was defined as any variation in results that had medical relevance and may have resulted in an alteration in medical care (e.g., active observation, diagnostic measures, or therapeutic measures). If a clinically significant change from the initial telemetry findings on Day 1 (approximately 30 minutes before the start of infusion) was noted, the clinically significant value and reason for clinical significance were documented on the AE page in the subject's eCRF. The subject was monitored continuously with additional assessments until follow-up was no longer medically necessary.

Physical Examination

Complete physical examinations and brief physical examinations were performed at the time points indicated in the schedule of events (Table 1). A complete physical examination (including an assessment for cutaneous erythema) was performed at screening and on Days 3, 14, and 140. A brief physical examination (including an assessment for cutaneous erythema) was performed at check-in (Day −1) and on Days 5, 29, and 85. The physical examination included height and weight at screening and weight only on other days.

A complete physical examination included assessments of the skin (including any signs of cutaneous erythema), head, ears, eyes, nose, throat, neck, thyroid, lungs, heart, cardiovascular system, abdomen, lymph nodes, and musculoskeletal system/extremities. Interim physical examinations were to be performed to evaluate AEs or clinical laboratory abnormalities.

A brief physical examination included assessments of the skin (including any signs of cutaneous erythema), lungs, cardiovascular system, and abdomen (liver, spleen).

Height and weight were measured and body mass index was calculated only at screening. Weight was measured at all other physical examination time points indicated in the schedule of events.

Dose Selection for Human Studies

The starting dose in this Phase 1, FIH study was 0.003 mg/kg, which was determined using the NOAEL from a 4-week, repeat-dose toxicology study in nonhuman primates, the closest and most relevant model to humans and applying an appropriate safety factor as well as from calculation of the minimum anticipated biological effect level (MABEL) for FB825, based on the in vitro and in vivo pharmacological data and toxicokinetic data.

The NOAEL for FB825 in the 4-week, repeat dose toxicology study in cynomolgus monkeys was considered to be 100 mg/kg. The equivalent human dose, calculated according to the Food and Drug Administration (FDA) Guidance for Industry: Estimating the Maximum Safe Starting Dose in Initial Clinical Trials for Therapeutics in Adult Healthy Volunteers (July 2005), is 38.8 mg/kg; after applying an appropriate safety factor to this (i.e., 100-fold), the maximum recommended starting dose in human subjects would be approximately 0.39 mg/kg.

The MABEL for FB825 was estimated to be 0.1 µg/mL. It was estimated that a single IV dose in human subjects of 0.003 mg/kg would result in systemic exposure to FB825 in the range from 0.06 µg/mL to 0.09 µg/mL; thus, the MABEL should not be exceeded during the study. Taking the higher figure of this range, the expected maximum circulating concentration of FB825 with this starting dose would be approximately $4.4 \times 10^4$-fold less than the $C_{max}$ for FB825 at the NOAEL (100 mg/kg/day) dose level in cynomolgus monkeys, which were administered a single IV dose of FB825 (Study 20031008). This provides a safety margin of $3.7 \times 10^4$-fold on a milligram per kilogram basis, over and above the human equivalent dose of 111.6 mg/kg at the NOAEL (300 mg/kg).

Results

This study evaluated the safety, tolerability, pharmacokinetics, and immunogenicity of single ascending doses of FB825 via IV injection in a randomized, placebo-controlled, double-blind study in healthy adult human subjects. The design and choice of the study population of the planned first-in-human (FIH) clinical Phase 1 study was based on the need to obtain initial safety, tolerability, PK, and immunological outcomes for FB825 for future clinical studies. Data was obtained according to the schedule of events presented in Table 1.

FB825 was Safely Administered to Human Subjects

Single, 1 hour, IV infusions of FB825 at doses of 0.003. 0.03, 0.3, 1.5, 5, and 10 mg/kg were safe and well tolerated by the healthy subjects in the clinical trial. There were no deaths and no subject discontinued due to a treatment emergent adverse event (TEAE). With the exception of decreased hemoglobin, upper respiratory tract infection, urinary tract infection, and gunshot wound, all TEAEs resolved by the end of the study.

There were no apparent treatment- or dose-related trends in clinical laboratory test results, vital sign measurements, 12-lead ECG results, or physical examination findings.

Total IgE Reduced by Administration of FB825

Figure 2:
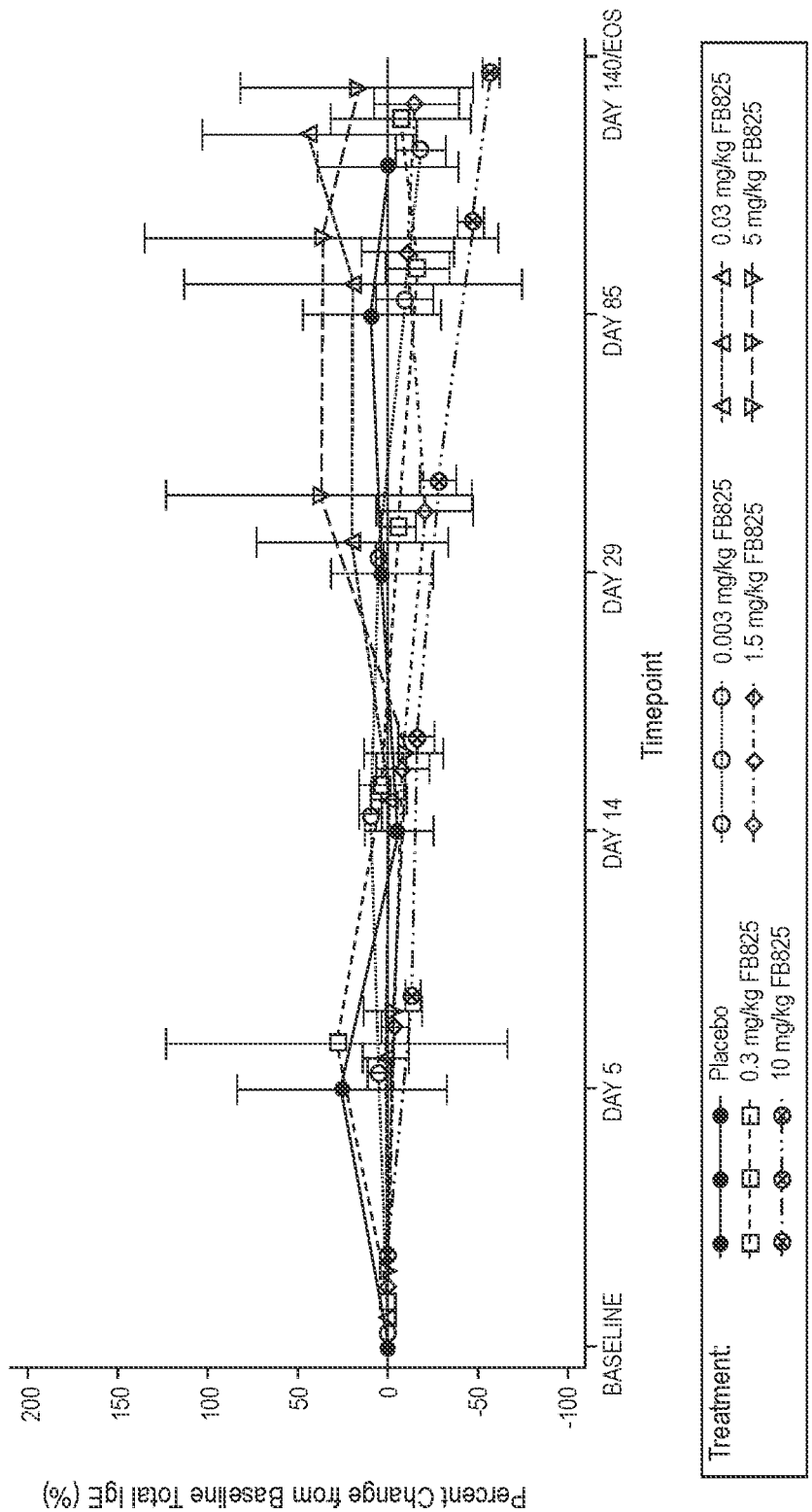
FIG. 2 is a diagram showing the mean (±SD) percent change from baseline in total IgE over time in human subjects treated by a single dose of FB825. Total IgE levels in blood samples obtained from the human subjects were determined. Baseline was defined as the last non-missing assessment (including repeated and unscheduled assessments) before study drug administration.

The total IgE was reduced at all postdose time points in the 1.5 and 10 mg/kg FB825 treatment groups. In the other doses (0.003, 0.03, 0.3, and 5 mg/kg FB825) and placebo treatment groups, the total IgE was reduced at some postdose time points but there were no overall trends (FIG. 1 and FIG. 2).

Figure 3:
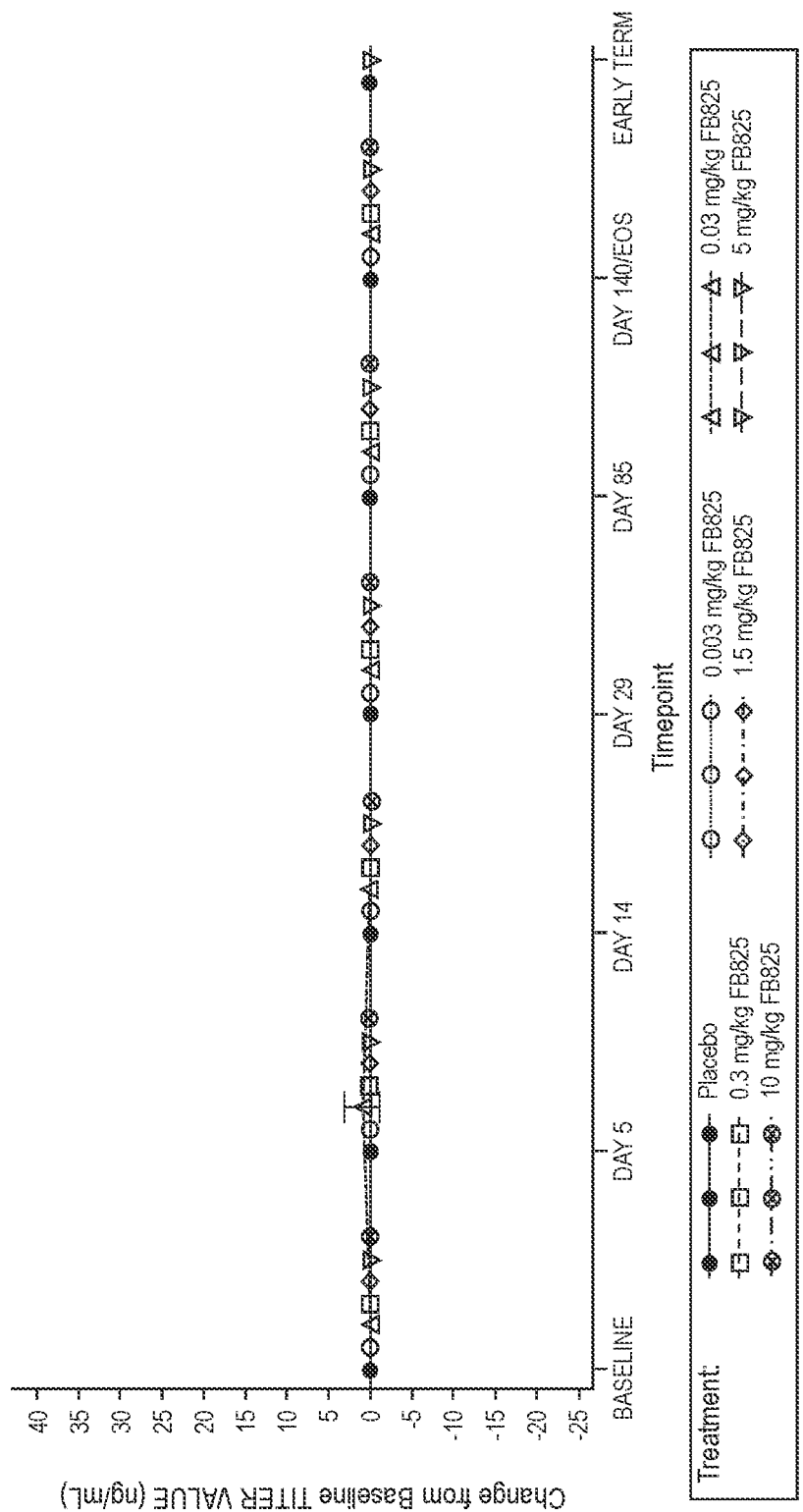
FIG. 3 is a diagram showing the mean (±SD) change from baseline in antidrug antibody (ADA) over time in human subjects treated by a single dose of FB825. ADA in blood samples obtained from the subjects was determined. Baseline is defined as the last non-missing assessment (including repeated and unscheduled assessments) before the study drug administration.

Only 4 subjects (1 each in the 0.03, 0.3, and 5 mg/kg FB825 and placebo treatment groups) had detectable ADA, where only 1 subject in the 0.03 mg/kg FB825 treatment group had reactive ADA (FIG. 3).

Example 3: An Open-Labeled Exploratory Study to Evaluate Safety and Efficacy of FB825 in Adults with Atopic Dermatitis The instant study is designed to evaluate the change from baseline in total IgE and allergen-specific IgE in patients having atopic dermatitis after IV administration of FB825 and to evaluate the clinical efficacy of these patients. This study also aims at evaluating the safety of FB825 in patients treated thereby, monitoring the changes in clinical hematology after the IV administration of FB825, and exploring changes from baseline in biomarkers, including thymus and activation regulated chemokine (TARC), Eotaxin-3, thymic stromal lymphopoietin (TSLP), periostin, IL-1a, IL-4, IL-5, IL-13, IL-16, IL-31, and M-CSF after the IV administration of FB825.

FB825 is a humanized monoclonal immunoglobulin G1 (IgG1) targeting the CεmX domain on human B lymphocytic cells expressing membrane-bound IgE (mIgE). FB825 can block the biological pathway of IgE synthesis, thus benefiting treatment of IgE-mediated allergic diseases. FB825 is formulated in an aqueous solution and given to a patient via a 1-hour IV infusion at 5 mg/kg.

The heavy chain (top) and light chain (bottom) amino acid sequence of FB825 in full-length format is provided below (including N-terminal signal peptide sequences). The heavy chain and light chain CDRs of FB825 (following the Kabat numbering scheme) are provided above in FIG. 4.

(SEQ ID NO: 11)
MEFGLSWLFLVAILKGVQCQVQLQESGPGLVKPSETLSLTCTVSGYSITS

DYAWNWIRQPPGKGLEWIGSISYSGITGYNPSLKSRVTISRDTSKNQFSL

KLSSVTAADTAVYYCARMGYDGLAYWGQGTLVTVSSASTKGPSVFPLAPS

SKSTSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEA

LHNHYTQKSLSLSPGK (SEQ ID NO: 12)
MRVPAQLLGLLLLWLPGARCDIVMTQTPLSLSVTPGQPASISCRSSQSIV

HSNGNTYLEWYLQKPGQSPQLLIYKVSNRFSGVPDRFSGSGSGTDFTLKI

SRVEAEDVGVYYCFQGSHVPPTFGGGTKVEIKRTVAAPSVFIFPPSDEQL

KSGTASVVCLLNNFYPREAKVQWKVDNALQSGNSQESVTEQDSKDSTYSL

SSTLTLSKADYEKHKVYACEVTHQGLSSPVTKSFNRGEC

Study Procedures

This is an open-labeled exploratory study to evaluate safety and efficacy of FB825 in adults with atopic dermatitis (AD). Approximately 12 human patients with atopic dermatitis (AD), who meet the criteria for study entry, were enrolled to the study. All eligible patients received FB825, 5 mg/kg, by 1-hour IV infusion on Day 1 and Day 85 (Table 2). Subjects were hospitalized after receiving FB825 on Day 1 and Day 85 and were discharged from the hospital next day for safety observation (at least 12 hours). Patients returned to the study site on Days 8, 15, 29, 57, 85, 92, 99, 113, 141, and 169 for the safety and efficacy, and biomarker evaluation (Table 2).

In some instance, patients may be asked to have site visit at Day 78 for blood sampling. The purpose of the blood sampling is to measure total IgE in order to determine if subjects need the second dose of FB825. Subjects with change from baseline in total IgE less than 50% at Day 78 may received the second dose of FB825 (5 mg/kg). Subjects with change from baseline in total IgE 50% at Day 78 may have the End of study visit at Day 85 and then complete the study For patients who receive the second dose of FB825, the data collected for the second dose may be analysis and summarized as same as those collected for the first dose. In some instances, patients received the second dose of FB825, 5 mg/kg, by 1-hour IV infusion on Day 85. Such patients were hospitalized before receiving FB825 on Day 85 and were discharged from the hospital next day for safety observation (at least 12 hours). The patients returned to the study site on Days 92, 99, 113, 141 and 169 for the safety and efficacy evaluation.

Serum total IgE and antigen-specific IgE were measured at scheduled visits and evaluated to explore the changes from baseline after the IV administration of 5 mg/kg FB825.

Patients were examined for clinical efficacy evaluation activities at scheduled visits, including Pruritus VisualAnalogue Scale (VAS), EczemaArea and Severity Index (EASI), Severity Scoring of Atopic Dermatitis Index (SCORAD), Investigator GlobalAssessment (IGA) for AD and Body Surface Area (BSA) involved in AD symptoms.

Safety data, including AEs and laboratory tests, were reviewed by the PI. The duration of subject participation the study, was approximately 24 weeks.

Selection of Study Population

Male or female subjects with atopic dermatitis were enrolled in a single study site. Approximately 15 subjects in total were enrolled to achieve at least 12 evaluable subjects.

Selection Criteria
(i) Main Inclusion Criteria

Male or female subjects between 20 and 65 years of age, inclusive.

The subject has a physician-confirmed diagnosis of chronic atopic dermatitis based on 3 years history of symptoms defined by the Eichenfield revised criteria of Hannifin and Rajka and supported by positive allergen-specific IgE at the screening visit.

Eczema Area and Severity Index (EASI) score ≥14 at the screening and baseline visits.

Investigator's Global Assessment (IGA) score ≥3 (5-point scale) at the screening and baseline visits.

≥10% body surface area (BSA) of AD involvement at the screening and baseline visits.

History of inadequate response to a stable (1 month) regimen of topical corticosteroids or calcineurin inhibitors as treatment for AD within 3 months before the screening visit. (The regimen of topical corticosteroids means medium to high potency, applied for at least 28 days or for the maximum duration recommended by product prescribing information.)

Patients must be applying stable doses of emollient provided for atopic dermatitis twice-daily for at least 7 days before the baseline visit.

Female subjects of childbearing potential must use at least two forms of birth control. One must be barrier protection (i.e., condom or female condom) and the other is one of acceptable method of birth control (i.e., diaphragm, intrauterine device, hormonal contraceptives, or abstinence) throughout the study. Subjects who are surgically sterile (i.e., hysterectomy, bilateral tubal ligation, or bilateral oophorectomy), or postmenopausal (defined as amenorrhea for 12 consecutive months and documented serum follicle stimulating hormone level>40 mU/mL) will be considered as no childbearing potential. All female subjects must have a negative serum pregnancy test prior to dosing. The subject must use the method of contraception mentioned above during the study period and in 16 weeks or 5 half-lives after the last dosing of FB825.

The subject has a body weight ≥40 kg at screening and a body mass index of 18.0 to 30.0 kg/m², inclusive.

The subject has a normal, as determined by the investigator, 12-lead electrocardiogram (ECG) with normal cardiac conduction parameters:
Heart rate between 45 and 100 bpm;
Fridericia-corrected QT interval (QTcF) ≤450 milliseconds (men) or ≤470 milliseconds (women); and
QRS interval lower than 120 milliseconds.
The subject is healthy, except atopic diseases, as determined by the investigator, on the basis of clinical laboratory test results performed at screening. If the results are outside the normal reference ranges, the subject may be included only if the investigator judges the abnormalities or deviations from normal not to be clinically significant. This determination must be recorded in the subject's source document and initialed by the investigator. This is not applicable to the laboratory abnormalities listed in the exclusion criterion (using the Division of Microbiology and Infectious Diseases criteria).
The subject is able to provide written informed consent.
The subject agrees to comply with all protocol requirements.

(ii) Main Exclusion Criteria

Female subjects who are pregnant or lactating.
The subject is on diet or with poor intake.
The subject has a history of heart arrhythmias (any clinically relevant).
The subject has a positive test result for hepatitis B surface antigen, hepatitis C virus antibody, or human immunodeficiency virus antibodies at screening.
The subject has a history of alcohol or drug abuse that would impair or risk the patients' full participation in the study, in the opinion of the investigator.
The subject is under judicial supervision or curatorship.
The subject has a clinically relevant, currently active or underlying gastrointestinal cardiovascular, nervous system, psychiatric, metabolic, renal, hepatic, respiratory (with the exception of uncomplicated allergic rhinitis), inflammatory, immunological, endocrine, diabetes, or infectious disease and ineligible to participate in the study judged by investigator.
The subject has any history of a previous anaphylactic reaction.
The subject has any condition that, in the opinion of the investigator, would compromise the study or the well-being of the subject or prevent the subject from meeting or performing study requirements.
The subject has received any immunoglobulin products or blood products within 3 months prior to dosing.
The subject has received a biologic product:
The subject has received any cell-depleting agents, not only limited to rituximab, within 6 months prior to dosing, or before the lymphocyte count returns to normal, whichever is longer.
The subject has received other biologics within 5 half-lives (if known) or 16 weeks, which is longer, prior to dosing).
The subject has one or more of the following laboratory abnormalities at screening as defined by Division of Microbiology and Infectious Diseases Adult Toxicity Table, 2007 [Laboratory values may be converted to equivalent standard units. Retesting of abnormal laboratory values that may lead to exclusion will be allowed once (without prior sponsor approval). Retesting will take place during an unscheduled visit in the screening phase (before baseline)]:
Aspartate aminotransferase or alanine aminotransferase (>2× upper limit of normal [ULN]) or higher;
Total bilirubin ≥1.5×ULN
Serum creatinine ≥1.6×ULN
Any other laboratory abnormality higher than or equal to grade 2 with the exception of IgE level, eosinophil counts, eosinophil cationic protein (ECP) and laboratory values mentioned above.
Laboratory values may be converted to equivalent standard units. Retesting of abnormal laboratory values that may lead to exclusion may be allowed once (without prior sponsor approval). Retesting may take place during an unscheduled visit in the screening phase (before baseline).
The subject has received any approved or unapproved (i.e., investigational) immunotherapy treatment within the past 3 months.
The subject has used any of the following classes of medication (prescription or over the counter):
Intranasal corticosteroid (e.g., fluticasone propionate) within 30 days prior to dosing.
Systemic corticosteroids (e.g., prednisone) within 30 days prior to dosing.
Leukotriene modifiers (e.g., montelukast) within 30 days prior to dosing.
Immunosuppressants (e.g., gold salts, methotrexate, azathioprine, cyclosporine) within the past 30 days prior to dosing.
Immunomodulating drugs (e.g., IFN-γ) within the past 30 days prior to dosing.
Anti-IgE (e.g., omalizumab) within the past 1 year prior to dosing.
Allergen immunotherapy within the past 1 year prior to dosing.
Orally inhaled corticosteroids (e.g., budesonide) within the past 30 days prior to dosing.
The subject has received phototherapy within 4 weeks prior to dosing.
The subject has received live vaccine within 12 weeks prior to dosing.
The subject has known or suspected history of immunosuppression, including history of opportunistic infections (e.g., TB) per investigator judgment.
The subject has history of malignancy within 5 years before the screening period.
High risk of parasite infection. Risk factors for parasitic disease (living in an endemic area, chronic gastrointestinal symptoms, travel within the last 6 months to regions where geohelminthic infections are endemic, and/or chronic immunosuppression) AND Evidence of parasitic colonization or infection on stool evaluation for ova and parasites. Stool ova and parasite evaluation will only be conducted in patients with risk factors and an eosinophil count more than twice the upper limit of normal subjects.

Study Treatments (i) Dosing and IV Administration of Study Treatment

Two doses of 5 mg/kg FB825 was given to subjects with atopic dermatitis. Subjects received FB825 by 1-hour IV infusion in the morning at Day 1 and Day 85. Fasting for at least 2 hours was required in some instance. Water intake is not allowed within 1 hour prior to dosing and 1 hour after dosing. The administered amount of FB825 can be adjusted based on subject's body weight, the appropriate amount of drug product was diluted with 250 mL 0.9% sodium chloride solution. FB825 was administered via IV route over 1 hour with the aid of a programmable volumetric infusion device. The final diluted product with 0.9% sodium chloride, after reconstitution, has to be used as soon as possible, and has to be used with 8 hours. The reconstituted FB825 can be stored at 2° C. to 25° C. for a maximum of 8 hours, prior to use.

(ii) Prior, Concomitant and Prohibited Medications

Prior Medications and Therapies

Information about prior medication taken by the subject within the 30 days before he or she provides informed consent was recorded in the subject's CRF.

Pre-Treatment/Concomitant Medication and Procedures

Any treatment (including nutritional supplements) or procedure administered from the time of signing of the ICF to the end of study visit is considered concomitant and was recorded in the CRF. This includes permitted medications ongoing at the time of consent.

The AD basal therapy during the study described below:

All patients are required to apply moisturizers at least twice daily for at least the 7 consecutive days prior to dosing and to continue the treatment throughout the study. All types of moisturizers are permitted, but patients may not initiate treatment with prescription moisturizers or moisturizers containing additives during the screening period or during the study.

Patients may continue using stable doses of prescription moisturizers or moisturizers containing additives, if initiated before the screening visit. Starting on day 1/baseline, all patients are required to initiate treatment with topical corticosteroid (TCS) using a standardized regimen according to the following guidelines:

Apply medium potency TCS daily to areas with active lesions. Low potency TCS should be used on areas of thin skin (face, neck, intertriginous, and genital areas, areas of skin atrophy, etc.) or for areas where continued treatment with medium potency TCS is considered unsafe.

After lesions are under control (clear or almost clear), switch from medium potency to low potency TCS and treat daily for 7 days, then stop.

If lesions return, reinstitute treatment with medium potency TCS, with the step-down approach described above upon lesion resolution.

For lesions persisting or worsening under daily treatment with medium potency TCS, patients may be treated (rescued) with high or super-high potency TCS, unless higher potency TCS are considered unsafe.

Monitor the patient for signs of local or systemic TCS toxicity and step down or stop treatment as necessary.

The type and amount of topical products used during the study were recorded. The amount of TCS used was determined by weighing the tube at each visit (see study reference manual for details).

It is recommended that patients use fluticasone propionate 0.05% cream, mometasone furoate 0.1% cream, or betamethasone valerate 0.06% cream as medium potency TCS, and hydrocortisone 1% ointment for low potency TCS.

If rescue with TCS is needed, it is recommended that patients use fluocinonide 0.05% cream, desoximetasone 0.25% ointment as high potency TCS, and clobetasol propionate 0.05% ointment for super high potency TCS.

Do not use moisturizers and TCS on the same areas at the same time during the day. On areas not treated with TCS, moisturizers will be applied twice daily—morning and evening.

Pre-treatment medication/procedures: medications taken or procedures performed prior to dosing.

Concomitant medication/procedures: medications taken or procedures performed following the IV administration of study drug through the EOS visit.

Prohibited Concomitant Medications:

Tropical tacrolimus and pimecrolimus

Systemic corticosteroids, unless the subjects are under rescue medication.

Leukotriene inhibitors

Allergen immunotherapy

Systemic treatment for AD with an immunosuppressive/immunomodulating substance (including, but not limited to, cyclosporine, mycophenolate-mofetil, IFN-γ, azathioprine, methotrexate, or biologics)

Treatment with a live (attenuated) vaccine

Traditional Chinese Medicine

Prohibited Concomitant Procedures:

Surgical procedures

Concomitant ultraviolet (UV) procedures (phototherapy [NBUVB, UVB, UVA1, or PUVA])

Tanning in a bed/booth is not allowed during the study

Patients are not allowed more than 2 bleach baths per week during study participation (iii) Handling of Infusion-Related or Allergic Reaction The IV administration of study drug must be performed under supervision of trained medical staff and where facilities to handle allergic reactions are available. If a subject experiences an infusion-related reaction, the subject must be treated symptomatically with supportive care, further monitoring, and appropriate medical therapy which may include antihistamines and/or corticosteroid if needed. The study infusion may be stopped and the subject would followed until the end of the study. The amount infused was recorded. Should a subject experience symptoms typical of an allergic reaction (eg, shortness of breath, anaphylaxis, urticaria, angioedema), then study drug IV administration should be discontinued immediately and permanently.

Suspected anaphylaxis should be assessed according to the clinical diagnostic criteria outlined by the National Institute of Allergy and Infectious Diseases which are provided in Appendix 12-2.

For these and other circumstances, subjects may receive appropriate medical treatment at the discretion of the investigator.

In case of allergic reactions, patients may be rescued with a prohibited medication or procedure to treat intolerable AD symptoms.

If medically necessary (i.e., to control intolerable AD symptoms), rescue treatment with systemic corticosteroids for AD at doss less than 1 mg/kg/day prednisolone and no more than 3 days may be provided to study patients after week 2.

Patients were subject to efficacy and safety assessments (e.g., disease severity scores, safety labs) immediately before administering any rescue treatment.

Study Procedures and Methods of Assessment

The following sections describe the study procedures and data to be collected. Subjects were assessed by the same investigator or site personnel whenever possible. The schedule and assessment is provided in Table 2. The baseline characteristics are provided in Table 3.

(i) Endpoints:
Primary Endpoint(s):
Change from baseline in total IgE at Day85 and day 169/End of Study (EOS).
Change from baseline in allergen-specific IgE at Day 85 and Day 169/EOS.
Endpoints for Biomarker:
Change from baseline in total IgE at Day 8, 15, 29, 57, 85, 92, 99, 113, 141 and 169.
Change from baseline in allergen-specific IgE at Day 8, 15, 29 and 57, 85, 92, 99, 113, 141, and 169. Change from baseline in biomarkers including thymus and activation regulated chemokine (TARC), Eotaxin-3, thymic stromal lymphopoietin (TSLP), periostin, IL-1a, IL-4, IL-5, IL-13, IL-16, IL-31 and M-CSF after IV administration of FB825 at Days 8, 15, 29, 57, 85, 92, 99, 113, 141, and 169.
Efficacy Endpoints:
Changes from baseline in Pruritus Visual Analogue Scale (VAS) at Days 8, 15, 29, 57, 85, 92, 99, 113, 141, and 169.
Changes from baseline in Eczema Area and Severity Index (EASI) at Days 8, 15, 29, 57, 85, 92, 99, 113, 141, and 169.
Changes from baseline in Severity Scoring of Atopic Dermatitis Index (SCORAD) at Days 8, 15, 29, 57, 85, 92, 99, 113, 141, and 169.
Changes from baseline in Investigator Global Assessment (IGA) for atopic dermatitis at Days 8, 15, 29, 57, 85, 92, 99, 113, 141, and 169.
Changes from baseline in Body Surface Area (BSA) involved in atopic dermatitis at Days 8, 15, 29, 57, 85, 92, 99, 113, 141, and 169.
Change from baseline in biomarkers including thymus and activation regulated chemokine (TARC), Eotaxin-3, thymic stromal lymphopoietin (TSLP), periostin, IL-1a, IL-4, IL-5, IL-13, IL-16, IL-31 and M-CSF after IV administration of FB825 at Days 8, 15, 29, 57, 85, 92, 99, 113, 141, and 169.
Safety was assessed by monitoring and recording of adverse events (AEs) and serious adverse event (SAEs); physical examination findings and vital sign measurements (systolic and diastolic blood pressures, heart rate, respiratory rate, and body temperature), clinical laboratory test results (hematology, coagulation, serum chemistry [including liver function tests, blood glucose level], and urinalysis); 12-lead ECG results.

(ii) Biomarker Assessments
Blood samples for the measurement of total, allergen-specific IgE, thymus and activation regulated chemokine (TARC), Eotaxin-3, thymic stromal lymphopoietin (TSLP), periostin, IL-1a, IL-4, IL-5, IL-13, IL-16, IL-31 and M-CSF was analyzed according to methodology described in a separate report.
Blood samples was collected. The actual sample collection time and sampling problems, if any, was recorded on the CRF. Approximately 5 mL sample of venous blood per sample was drawn at the following time points:
Total Immunoglobulin/Allergen-specific IgE:
Screening period: at any time
Day 1, and 85: (In 2 hours before the start of infusion)
Days 8, 15, 29, 57, 92, 99, 113, and 141, and 169 after IV administration of FB825 at any time on the day.
TARC, Eotaxin-3, TSLP, periostin, IL-1a, IL-4, IL-5, IL-13, IL-16, IL-31 and M-CSF:
Day 1 and 85 in 2 hours before the start of infusion, and at any time on Days 8, 15, 29, 57, 92, 99, 113, 141, and 169.

(iii) Clinical Efficacy Assessments
Pruritus Visual Analogue Scale (VAS).
The pruritus visual analogue scale (VAS) of SCORAD was applied for the measurement of pruritus. Patients were asked to assign a numerical score representing the intensity of their symptoms on a scale from 0 to 10, with 0 for having no symptoms and 10 having worst symptoms. Subjects were asked to perform the measurement at screening, Day 1 and 85 before dosing, Day 2 and Day 86 before discharge, and any time of Day 8, 15, 29, 57, 92, 99, 113, 141, and 169.
Severity Scoring of Atopic Dermatitis Index (SCORAD)
The SCORAD (Index) is the validated scoring system in atopic dermatitis (AD). To measure the extent of AD, the rule of nines is applied on a front/back drawing of the patient's inflammatory lesions. The extent can be graded from 0 to 100. The intensity part of the SCORAD consists of 6 items: erythema, oedema/papulation, excoriations, lichenification, oozing/crusts and dryness. Each item can be graded on a scale from 0 (absent) to 3 (severe). The subjective items include daily pruritus and sleeplessness. The SCORAD Index formula is: $A/5+7B/2+C$. In this formula A is defined as the extent (0-100), B is defined as the intensity (0-18) and C is defined as the subjective symptoms (0-20). The maximal score of the SCORAD Index is 103. Subjects were asked to perform the measurement at screening, Day 1, and 85 before dosing, Day 2 and Day 86 before discharge, and any time of Day 8, 15, 29, 57, 92, 99, 113, 141, and 169.
Eczema Area and Severity Index (EASI)
The EASI scoring system uses a defined process to grade the severity of the signs of eczema and the extent affected. Extent and severity of signs of eczema was evaluated in four body regions and the total score is the sum of the four regions scores adjusted with multipliers. The EASI score is ranged from 0-72. Subjects were asked to perform the measurement at screening, Day 1 and 85 before dosing, Day 2 and Day 86 before discharge, and any time of Day 8, 15, 29, 57, 92, 99, 113, 141, and 169.
Investigator Global Assessment (IGA) for AD
IGA allows investigators to assess overall disease severity at one given time point, and it consists of a 5-point severity scale from clear to very severe disease (0=clear, 1=almost clear, 2=mild disease, 3=moderate disease, and 4=severe disease). Subjects were asked to perform the measurement at screening, Day 1 and 85 before dosing, Day 2 and Day 86 before discharge, and any time of Day 8, 15, 29, 57, 92, 99, 113, 141, and 169.
BSA Involved in AD Symptoms
It was measured as part A (Extent) of SCORAD. Subjects were asked to perform the measurement at screening, Day 1 and 85 before dosing, Day 2 and Day 86 before discharge, and any time of Day 8, 15, 29, 57, 92, 99, 113, 141, and 169.

(iv) Safety Assessments
Safety was assessed by monitoring and recording of Adverse Event (AEs), Serious Adverse Event (SAEs), physical examination findings and vital sign measurements (systolic and diastolic blood pressures, heart rate, respiratory rate, and oral body temperature), clinical laboratory test results (hematology, coagulation, serum chemistry [including liver function tests], and urinalysis), and 12-lead ECG results. The overall summary of numbers of patients with adverse events through the 15-168 days treatment period-SAF is provided in Table 4.

Adverse Events

The Adverse Event section (Section 7) describes the Adverse Event (SAEs), Serious Adverse Event (SAEs) and Adverse Events of Special Interest were collected during the study.

Physical Examinations

A complete physical examination was performed at the time points indicated in the schedule of events.

A complete physical examination includes assessment of skin (including any signs for cutaneous erythema), head, ears, eyes, nose, throat, neck, thyroid, lungs, heart, cardiovascular system, abdomen, lymph nodes, and musculoskeletal system/extremities. Interim physical examinations were performed at the discretion of the investigator, if necessary, to evaluate AEs or clinical laboratory abnormalities. Height and weight was measured and body mass index will be calculated at screening only. Weight was also measured at all other physical examination time points as indicated in the schedules of events for the study. Body weight was recorded in kilograms (kg) to 1 decimal place in indoor clothing (without coat and shoes) and body height (without shoes) was measured in centimeters (cm) without decimal places.

Vital Sign Measurements

Vital sign measurements include systolic and diastolic blood pressures, heart rate, respiratory rate, and body temperature. The subject was seated for at least 5 minutes before all measurements are taken. Vital signs were measured at the time points indicated in the schedule of events.

When procedures are overlapping and occurring at the same time point, the order of procedures should be vital sign measurements and then ECGs.

The investigator may determine whether any of the vital sign measurements are clinically significant or not clinically significant. Clinical significance is defined as any variation in results that has medical relevance and may result in an alteration in medical care (e.g., active observation, diagnostic measures, or therapeutic measures). If a clinically significant change from the screening values is noted, the clinically significant value and reason for clinical significance was documented in the AE page of the subject's CRF. The investigator may continue to monitor the subject with additional assessments until the value has reached the reference range or the value at screening or until the investigator determines that follow-up is no longer medically necessary.

Clinical Laboratory Testing

Clinical laboratory tests were performed by local site. Blood and urine were be collected under fasting conditions (fasted for approximately 2 or more hours) at the time points indicated in the schedule of events.

The following hematology, coagulation, serum chemistry (including liver function and thyroid function tests), urinalysis assessments were performed:

Hematology: Hematocrit (Hct), hemoglobin (Hb), mean corpuscular hemoglobin (MCH),—mean corpuscular hemoglobin concentration (MCHC), mean corpuscular volume (MCV), platelet count, red blood cell (RBC) count, and WBC and differential count (absolute and percent).

Coagulation: International normalized ratio (INR), partial thromboplastin time (PTT), and -prothrombin time (PT)

Serum Chemistry: ALT, albumin, alkaline phosphatase, amylase, anion gap, AST, bicarbonate, bilirubin (total and direct), blood urea nitrogen (BUN), calcium, carbon dioxide, chloride, cholesterol (total, high-density lipoprotein, and calculated low-density lipoprotein), creatine phosphokinase, creatinine, gamma-glutamyl-transferase (γ-GT), globulin, glucose, lactate dehydrogenase (LDH), lipase, magnesium, phosphorus, potassium, sodium, total protein, triglycerides, troponin I or T, and uric acid.

Thyroid Function: Free T4 and thyroid-stimulating hormone

Urinalysis: Appearance, bilirubin, color, glucose, ketones, leukocyte esterase, microscopy (performed if dipstick is positive; includes bacteria, casts, crystals, epithelial cells, red blood cells, and white blood cells), nitrites, occult blood, pH, protein, specific gravity, turbidity, and urobilinogen A serum pregnancy test (β-human chorionic gonadotropin) will be performed on all female subjects with potential of children bearing at screening and confirmed result prior to dosing. Urine pregnancy tests were performed on Days 8, 15, 29, 57, 85, 92, 99, 113, 141, and 169. For female subjects who were postmenopausal, a serum follicle-stimulating hormone test was performed at screening.

Hepatitis B surface antigen, hepatitis C virus antibody, and human immunodeficiency virus antibody will be assessed at screening.

Abnormal clinical laboratory values were flagged as either high or low (or normal or abnormal) based on the reference ranges for each laboratory parameter. The investigator may determine whether any of the abnormally high or low results are clinically significant or not clinically significant. Clinical significance is defined as any variation in results that has medical relevance and may result in an alteration in medical care (e.g., active observation, diagnostic measures, or therapeutic measures). If a clinically significant change from the screening value is noted, the clinically significant value and reason for clinical significance may be documented in the AE page of the CRF. The investigator may continue to monitor the subject with additional assessments until the values have reached the reference range or the values at screening or until the investigator determines that follow-up is no longer medically necessary.

Clinically significant laboratory values for individual subjects were listed. A summary for the number and percentage of subjects with clinically significant laboratory values at any time point was presented.

Electrocardiograms

Single 12-lead ECGs were obtained after the subject has been in the supine position for at least 5 minutes at the time points indicated in the schedule of events. Electrocardiogram assessments include comments on whether the tracings are normal or abnormal, rhythm, presence of arrhythmia or conduction defects, morphology, any evidence of myocardial infarction, or ST segment, T wave, and U wave abnormalities. In addition, measurements of the following intervals will be measured and reported: RR interval, PR interval, QRS width, QT interval, and QTcF.

Adverse Events

The overall summary of number of patients with adverse events through the 15-168 days treatment period-SAF is provided in Table 4.

(i) Definitions

Adverse Event (AE)

An AE is defined as any untoward medical occurrence associated with the use of a drug in humans, whether or not considered drug related. Subjects will be instructed to contact the investigator at any time during the study period if any symptoms develop.

A TEAE is defined as any event not present before exposure to study drug or any event already present that worsens in intensity or frequency after exposure.

An adverse reaction is any AE caused by a drug. Adverse reactions are a subset of all suspected adverse reactions for which there are reasons to conclude that the drug caused the event.

A suspected adverse reaction is any AE for which there is a reasonable possibility that the study drug caused the AE. For the purposes of investigational new drug safety reporting, "reasonable possibility" means that there is evidence to suggest a causal relationship between the study drug and the AE. A suspected adverse reaction implies a lesser degree of certainty about causality than adverse reaction, which means any AE caused by a study drug.

An AE or suspected adverse reaction is considered "unexpected" if it is not listed in the IB or at the specificity or severity that has been observed with the study drug being tested; or, if an IB is not required or available, is not consistent with the risk information described in the general investigational plan or elsewhere in the current application. For example, under this definition, hepatic necrosis would be unexpected (by virtue of greater severity) if the IB referred only to elevated hepatic enzymes or hepatitis. Similarly, cerebral thromboembolism and cerebral vasculitis would be unexpected (by virtue of greater specificity) if the IB listed only cerebral vascular accidents. "Unexpected," as used in this definition, also refers to AEs or suspected adverse reactions that are mentioned in the IB as occurring with a class of drugs or as anticipated from the pharmacological properties of the drug, but are not specifically mentioned as occurring with the particular drug under investigation.

Serious Adverse Event (SAE)

An AE or suspected adverse reaction is considered an SAE if, in the view of either the investigator or sponsor, it results in any of the following outcomes:
  Death
  Life-threatening AE
  Inpatient hospitalization or prolongation of existing hospitalization
  Persistent or significant incapacity or substantial disruption of the ability to conduct normal-life functions
  Congenital anomaly or birth defect
  Important medical events that may not result in death, be life threatening, or require hospitalization may be considered serious when, based upon appropriate medical judgment, they may jeopardize the subject and may require medical or surgical intervention to prevent one of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse.

An AE or suspected adverse reaction is considered "life threatening" if, in the view of either the investigator or sponsor, its occurrence places the subject at immediate risk of death. It does not include an AE or suspected adverse reaction that, had it occurred in a more severe form, might have caused death.

Adverse Events of Special Interest

Adverse events of special interest include the following events:
  Any subject experiences a treatment-emergent AE (TEAE) of anaphylaxis
  Any subject experiences an SAE (Section 7.1.2)
  Any subject experiences a persistent QT prolongation (>500 milliseconds, or ≥60 milliseconds change from baseline) for at least 30 minutes or ischemic changes on repeated ECGs, or persistent symptomatic arrhythmia
  Hypersensitivity reactions including anaphylaxis, thyroid abnormalities, cutaneous erythema, thrombocytopenia, anemia, hemolysis, neutropenia, hepatotoxicity, and nephrotoxicity.

The following laboratory parameters are encountered in any individual subject:
  ALT or AST ≥5×ULN
  Bilirubin ≥2×ULN
  Platelet count grade 1≤99.999*10⁹/L
  Hemoglobin ≤105 g/L
  Absolute neutrophil count grade 1≤1.5*10⁹/L
  Blood urea nitrogen or creatinine rise to >2×ULN (ii) Eliciting of Adverse Events The investigator is responsible for ensuring that all AEs and SAEs are recorded in the CRF and reported to Fountain. Adverse events were assessed from the time of screening period until completion of all study procedures and discharge from the study.

At every study visit or assessment, subjects were asked a standard question to elicit any medically-related changes in their well-being. They were also asked if they had been hospitalized, had any accidents, used any new medications, or changed concomitant medication regimens (both prescription and over-the-counter medications).

In addition to subject observations, AEs were documented from any data collected in the AE page of the CRF (eg, laboratory values, physical examination findings, and ECG changes) or other documents that are relevant to subject safety.

Assessment for Severity The severity (or intensity) of an AE using the Common Terminology Criteria for Adverse Events (CTCAE) was used for infusion reaction severity grading.
  Grade 1 Mild: Transient or mild discomfort (<48 hours); no medical intervention/therapy-required.
  Grade 2 Moderate: Mild to moderate limitation in activity—some assistance may be needed; no or minimal medical intervention/therapy required.
  Grade 3 Severe: Marked limitation in activity, some assistance usually required; medical intervention/therapy required, hospitalization possible.
  Grade 4 Life threatening: Extreme limitation in activity, significant assistance required; significant medical intervention/therapy required, hospitalization or hospice care probable.

Changes in the severity of an AE should be documented to allow an assessment of the duration of the event at each level of intensity to be performed. An AE characterized as intermittent requires documentation of onset and duration of each episode.

7.3.2 Assessment of Causality

The investigator's assessment of an AE's relationship to study drug is part of the documentation process but is not a factor in determining what is or is not reported in the study.

The investigator assessed causality (i.e., whether there is a reasonable possibility that the study drug caused the event) for all AEs and SAEs. The relationship was characterized using the following classification:

Unrelated: This relationship suggests that there is no association between the study drug and the reported event.

Possible: This relationship is based on evidence suggesting a causal relationship between the study drug and the AE, i.e., there is a reasonable possibility that the drug caused the event. The event follows a reasonable temporal sequence from the time of drug IV administration or follows a known response pattern to the study drug, but could also have been produced by other factors.

Probable: This relationship suggests that a reasonable temporal sequence of the event with drug IV administration exists and, based upon the known pharmacological action of the drug, known or previously reported adverse reactions to the drug or class of drugs, or judgment based on the investigator's clinical experience, the association of the event with the study drug seems likely.

Definite: This relationship suggests that a definite causal relationship exists between drug IV administration and the AE, and other conditions (concurrent illness, progression/expression of disease state, or concurrent medication reaction) do not appear to explain the event.

Statistical Analysis (i) General Statistics

Details of all statistical analyses were described in a statistical analysis plan. All data collected was presented in data listings. Data from subjects excluded from an analysis population was presented in the data listings but not included in the calculation of summary statistics.

For categorical variables, frequencies and percentages were presented. Continuous variables were summarized using descriptive statistics (number of subjects, mean, median, SD, minimum, and maximum).

Baseline demographic and background variables were summarized by dose and overall for all subjects. The number of subjects who enroll in the study and the number and percentage of subjects who complete the study was presented. Frequency and percentage of subjects who withdraw or discontinue from the study, and the reason for withdrawal or discontinuation, was also be summarized. Analysis for this study was demonstrated with descriptive statistics for each period and group. No significance test was applied.

A statistical analysis plan (SAP) was written to address statistical analysis work in detail. The clinical database lock may occur after all data are reconciled (i.e., "cleaned") after the last patient completes the study.

(ii) Sample Size Calculations

A total of approximately 12 evaluable subjects were planned for this study. The sample size for this study is based on clinical and practical considerations and not on a formal statistical power calculation.

(iii) Analysis Sets

Full Analysis Set (FAS) is defined as subjects who received at least 1 dose of study drug. All efficacy evaluation will be performed in FAS population.

The Safety population is defined as subjects who received at least 1 dose of study drug. All safety evaluation will be performed in safety population.

(iv) Statistical Analysis

Biomarker Analyses

Concentration and change from baseline in total and allergen-specific IgE and biomarkers listed as endpoints was summarized by visit and presented graphically. Change from baseline in total and allergen-specific IgE was be summarized by the baseline total IgE concentration (serum IgE>1500 IU/mL or serum IgE ≤1500 IU/mL) and given FB825 doses (1 dose or 2 doses).

In subjects who receive the second dose of FB825, the data collected for the second dose were analysis and summarized as same as those collected for the first dose.

Clinical Efficacy Analysis

The evaluation index was assessed by PI or co-PI during every visit for each subject. The clinical endpoints were analyzed using descriptive statistic (mean of EASI, SCORAD, IGA, VAS, and BSA; SD, CV, number of subjects) by visit time points and given FB825 doses (1 dose or 2 doses).

The change of mean index versus scheduled visit time profiles was presented graphically, In subjects who receive the second dose of FB825, the data collected for the second dose was analysis and summarized as same as those collected for the first dose.

Safety Analyses

Adverse events were coded by preferred term and system organ class using the latest version of the Medical Dictionary for Regulatory Activities and summarized by treatment, dose level, and overall. Adverse events were also summarized by severity, relationship to study drug, SAEs, and AEs leading to discontinuation of study drug.

Actual values and changes from baseline for clinical laboratory test results, vital sign measurements, and 12-lead ECG results were summarized by treatment and dose at each time point using descriptive statistics (number of subjects, mean, SD, median, minimum, and maximum). Shift tables were generated for clinical laboratory test results. Clinical laboratory data, vital sign measurements, 12-lead ECG results, and physical examination findings were presented in data listings.

(v) Handling of Missing Data

Concentrations that are below the limit of quantification (BLQ) were treated as zero for descriptive statistics. Mean BLQ concentrations will be presented as BLQ, and the SD and CV were reported as not applicable. Missing concentrations will be excluded from the calculations.

Last observation carry forward (LOCF) was applied to handle missing data. No imputation will be available for safety data.

(vi) Data Quality Assurance

All aspects of the study were monitored for compliance with applicable government regulations with respect to current International Conference on Harmonisation (ICH) harmonized tripartite guideline E6 (R1): Good Clinical Practice and current standard operating procedures. There may be an internal quality review audit of the data and additional reviews by the clinical monitor.

TABLE 2

Schedule of Event and Assessment

| Study Day(s) | Screening −23 to −1 | Dose 1 FB825 | | | | | | Dose 2 FB825 | | | | | | |
|---|---|---|---|---|---|---|---|---|---|---|---|---|---|---|
| | | Day 1[a] | Day 2 | Day 8 (±1) | Day 15 (±1) | Day 29 (±2) | Day 57 (±2) | Day 85[a] (±3) | Day 86 | Day 92 (±1) | Day 99 (±1) | Day 113 (±2) | Day 141 (±2) | Day 169/EOS[b] (±3) |
| Informed consent | X | | | | | | | | | | | | | |
| Inclusion/Exclusion criteria | X | X | | | | | | | | | | | | |
| Medical history | X | | | | | | | | | | | | | |
| Physical examination | X | X | | X | X | X | X | X | | X | X | X | X | X |
| Vital sign measurements [c,d] | X | X | X | X | X | X | X | X | X | X | X | X | X | X |
| 12-Lead Electrocardiogram [e] | X | X | X | X | X | X | | X | X | X | X | X | | X |
| AD symptom evaluation [f] | X | X | X | X | X | X | X | X | X | X | X | X | X | X |
| Serology [g] | X | | | | | | | | | | | | | |
| Clinical laboratory testing [h] | X | X | X | X | X | X | X | X | X | X | X | X | X | X |
| Thyroid function testing | X | X | | | X | X | | X | | | X | X | | X |
| Urine drug, and blood alcohol test | X | X[m] | | | | | | X | | | | | | X |
| Pregnancy test (female subjects) [i] | X | X | | X | X | X | X | X | | X | X | X | X | X |
| Serum FSH [j] | X | | | | | | | | | | | | | |
| Admission to clinic | | X | | | | | | X | | | | | | |
| Study drug IV administration | | X | | | | | | X | | | | | | |
| Total Immunoglobulin/Allergen-specific IgE [k] | X | X | | X | X | X | X | X | | X | X | X | X | X |
| Biomarker Assessments [l] | | X | | X | X | X | X | X | | X | X | X | X | X |
| Adverse events assessment | X | X | X | X | X | X | X | X | X | X | X | X | X | X |
| Prior/Concomitant medications | X | X | X | X | X | X | X | X | X | X | X | X | X | X |
| Discharge from clinic | | | X | | | | | | X | | | | | |

Abbreviations: ALT, alanine aminotransferase;
AST, aspartate aminotransferase;
EOS, end of study;
FSH, follicle-stimulating hormone;
Ig, immunoglobulin.
[a]Subjects will check into the clinic on Day 1 and Day 85 and have check-in procedures performed.
[b]Subjects early withdraw from the study will be requested to have an EOS visit and perform required activities.
[c] Vital sign measurements (systolic and diastolic blood pressures, heart rate, respiratory rate, and body temperature) will be obtained at screening; Day 1, and 85 before the start of infusion and all study visits. Vital sign measurements will be obtained at 1.25 (end of infusion), 2, 4, 8 hours (±5 minutes in each time points) after the start of the infusion on Day 1, and Day 85,and prior to discharge on Day 2 and Day 86. During the infusion, vital sign measurements will be obtained every 15 minutes (±5 minutes).
[d] When procedures are overlapping and occurring at the same time point, the order of procedures should be vital sign measurements and then ECGs.
[e] Twelve-lead electrocardiograms will be obtained at screening; on Day 1 and Day 85 within 2 hours before the start of infusion and at 1.25 (end of infusion, ±5 minutes) 8 hours (±5 minutes) after the start of the infusion; prior to discharge; and all other study visits, except Day 57, and 141.
[f] AD symptom evaluation is determined by VAS, EASI, SCORAD, IGA, and BSA. These are evaluated by Investigator at screening; on Day 1 prior to dosing, and all other study visits.
[g] Serology testing will include hepatitis B surface antigen, hepatitis C virus antibody, and human immunodeficiency virus antibodies.
[h] Clinical laboratory tests (hematology, coagulation, serum chemistry [including liver function tests and glucose test], and urinalysis) will be performed at screening; on Day 1 and Day 85 before the start of infusion and at 1.25 (end of infusion, ±5 minutes), 8 hours (±5 minutes) after the start of the infusion; prior to discharge, and all other study visits.
[i] A serum pregnancy test will be performed for females of childbearing potential only at screening and at the end-of-study visit. Urine pregnancy tests will be performed on all other study visits, in Day 1 only to confirm the results, no need to have a test again.
[j] Female subjects who are postmenopausal will have a serum FSH test at screening.
[k] Blood samples for the measurement of total immunoglobulin/Allergen-specific immunoglobulin E will be collected at screening, on Day 1 before the start of infusion); and on all other study visits.
[l] Blood samples for the measurement of biomarkers including thymus and activation regulated chemokine (TARC), Eotaxin-3, thymic stromal lymphopoietin (TSLP), periostin, IL-1 , IL-4, IL-5, IL-13, IL-16, IL-31 and M-CSF will be collected at Day 1 and 85 (in 2 hours before the start of infusion), and on Days 8, 15, 29, 57, 92, 99, 113, and 141.
[m]The X in Day 1 of Urine drug and blood alcohol test means to confirm the results, no need to have a test again

TABLE 3

Baseline Characteristics

| Score | | FB825 5 mg/Kg q12w + TCS (n = 12) | |
|---|---|---|---|
| | range | median (IQR)/n (%) | mean |
| Age, years, median (IQR) | — | 31.5 (25, 34.5) | 30.8 |
| Male, n (%) | — | 6 (50) | |
| EASI, median (IQR) | 0-72 | 27.4 (17.9, 31) | 25.8 |
| SCORAD, median (IQR) | 0-103 | 60.5 (48.4, 64.8) | 57.9 |
| Patients with IGA = 4, n (%) | 0-4 | 8 (67) | 3.7 |

TABLE 3-continued

Baseline Characteristics

| Score | range | FB825 5 mg/Kg q12w + TCS (n = 12) median (IQR)/n (%) | mean |
|---|---|---|---|
| SCORAD VAS pruritus domain, median (IQR) | 0-10 | 4.95 (3.95, 6.1) | 5.0 |
| CORAD VAS sleep domain, median (IQR) | 0-10 | 4.5 (1.0, 5.9) | 3.9 |
| % BSA, median (IQR) | 0-100 | 42.5 (27.5, 55.8) | 43.8 |
| IgE, median (IQR) | — | 2828.9 (1534.95, 4029.4) | 3379.7 |

TABLE 4

Overall Summary of Number of Patients With Adverse Events Through the 15-168 days Treatment Period-SAF

| Patients with, n (%): | FB825 5 mg/Kg q12w + TCS (n = 12) |
|---|---|
| Any TEAE | 6 (50) |
| Any drug-related TEAE (possible) | 3 (25) |
| Any TEAE causing discontinuation of study drug | 0 |
| Conjuctivitisa | 1 (8) |
| Herpes viral infections | 2 (20) |
| Upper respiratory infection | 5 (42) |
| Rhinorrhea | 1 (8) |
| Asthma attack | 1 (8) |
| Fever | 1 (8) |
| Cough | 1 (8) |
| prolonged QTC | 1 (8) |
| Any death | 0 |
| Any TE SAE | 0 |
| Any drug-related TE SAE | 0 |
| Any TE SAE causing discontinuation of study drug | 0 |
| Any Severe TEAE | 0 |

Results

This is an open-labeled exploratory study to evaluate safety and efficacy of FB825 in adults with atopic dermatitis (AD). 12 eligible human patients with AD were enrolled in the study and received FB825, 5 mg/kg, by 1-hour IV infusion on Day 1 and Day 85. Patients were scheduled to return to the study sites according to the schedule of events presented in Table 2 for the safety and efficacy evaluation. FB825 was Safely Administered to Human Subjects with AD FB825 was administered to the patients via IV infusion over 1 hour at 5 mg/kg on days 1 and 85. There were no deaths and no subject discontinued due to a treatment emergent adverse event (TEAE) or treatment emergent severe adverse event (TE SAE). Six subjects developed TEAE, three of which are possibly drug related. Five subjects developed upper respiratory infection and two subjects contracted Herpes viral infections. Only one subject was reported to have developed one of the following: conjunctivitis, rhinorrhea, asthma attack, fever, cough or prolonged QTC. (Table 4)

There were no apparent treatment or dose-related trends in clinical laboratory test results, vital sign measurement, 12-lead ECG results, or physical examination findings.

Efficacy

Efficacy of FB825 was determined by recording the changes from baseline in Eczema Area and Severity Index (EASI), Investigator Global Assessment (IGA), Severity Scoring of Atopic Dermatitis Index (SCORAD) and Pruritus Visual Analogue Scale (VAS) at Days Day 1 and 85 before dosing, Day 2 and Day 86 before discharge, and any time of Day 8, 15, 29, 57, 92, 99, 113, 141, and 169. Baseline demographic and background variables will be summarized by dose and overall for all subjects in Table 3.

(i) EASI was Reduced Compared to Baseline by FB825

Figure 5:
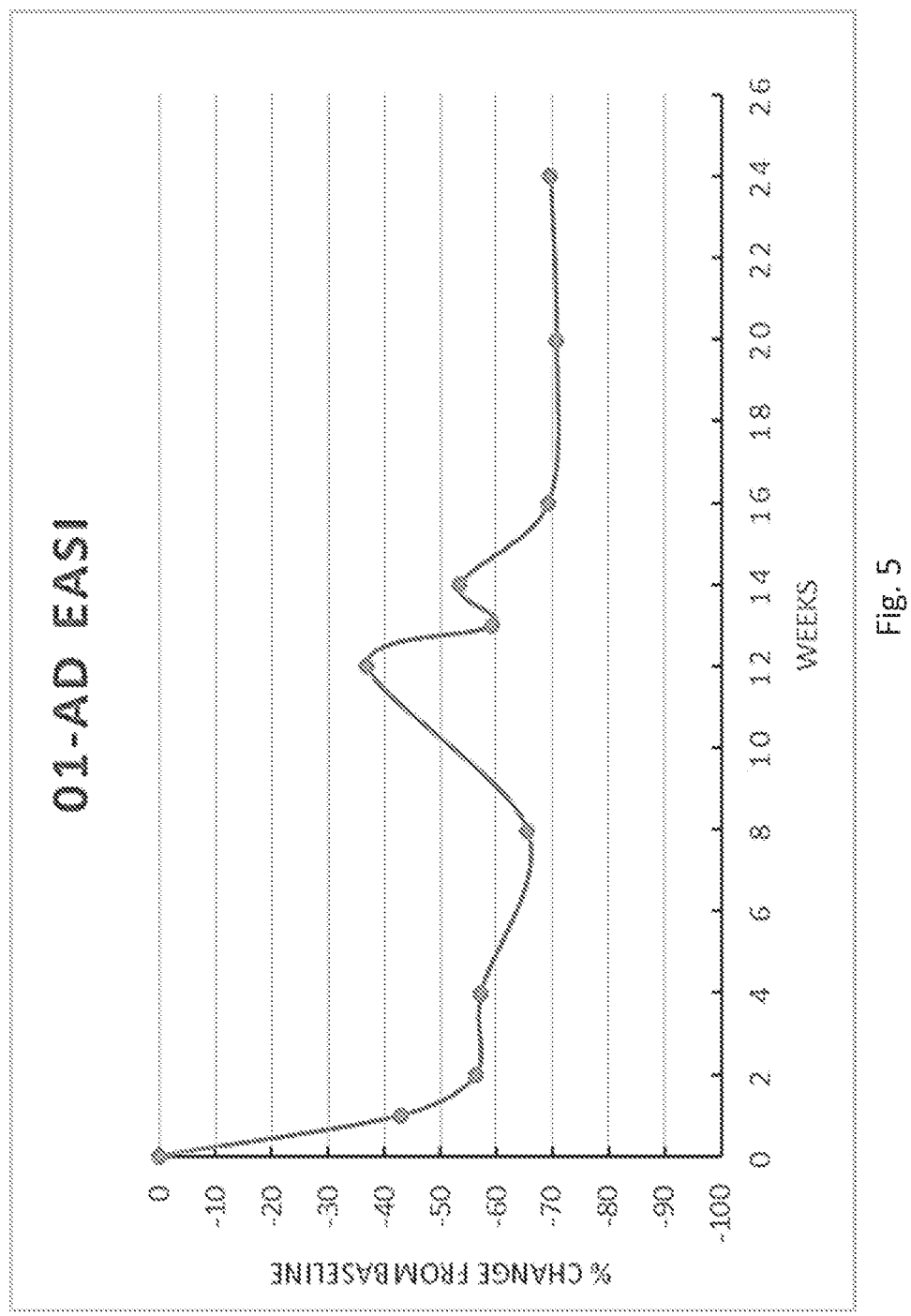
FIG. 5 is a diagram showing the percentage change from baseline in Eczema Area and Severity Index (EASI) at Days 8, 15, 29, 57, 85, 92, 99, 113, 141, and 169 in the Open-LabeleExploratory Study to Evaluate Safety and Efficacy of FB825 in Adults with Atopic Dermatitis.

Subjects showed progressively reduced EASI after FB825 administration on Day 1 till approximately Day 55 (approximately 65% reduction). EASI score started rising after Day 55 until the second FB825 administration on Day 85 but it is still approximately 40% less compared to baseline. Subjects showed further EASI reduction to approximately 70% reduction on Day 113 and maintained the level till the end of study (EOS). (FIG. 5).

(ii) IGA was Reduced Compared to Baseline by FB825

Figure 6:
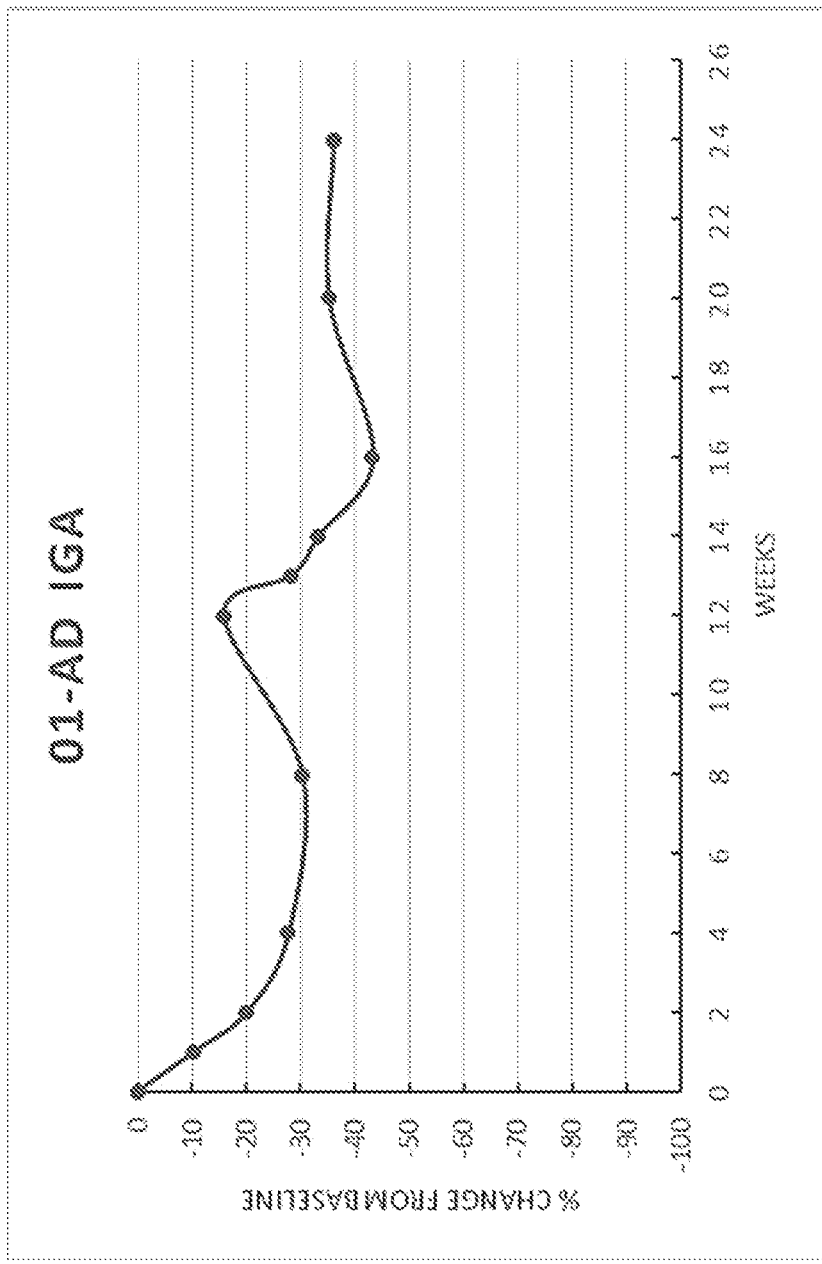
FIG. 6 is a diagram showing the percentage change from baseline in Investigator's Global Assessment (IGA) at Days 8, 15, 29, 57, 85, 92, 99, 113, 141, and 169 in the Open-LabeleExploratory Study to Evaluate Safety and Efficacy of FB825 in Adults with Atopic Dermatitis.

Subjects showed progressively reduced IGA after FB825 administration on Day 1 till Day 55 (approximately 30% reduction). IGA score started rising after Day 55 until the second FB825 administration on Day 85 but it is still approximately 15% less compared to baseline. Subjects showed further IGA reduction to approximately 45% reduction at the lowest on Day 113 and maintained the reduction level of 35% compared to baseline till the end of study (EOS). (FIG. 6).

(iii) SCORAD was Reduced Compared to Baseline by FB825

Figure 7:
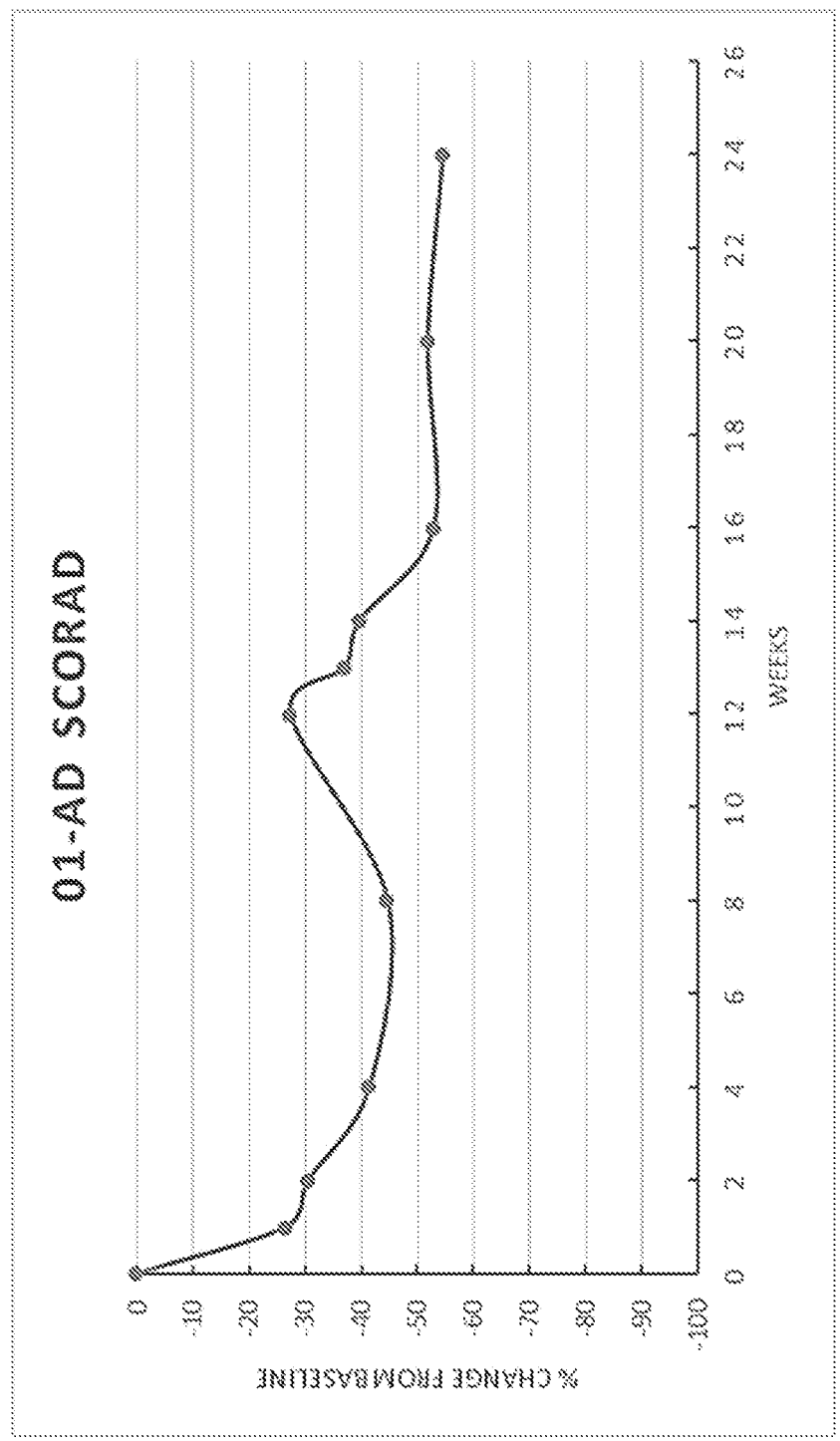
FIG. 7 is a diagram showing the percentage change from baseline in Severity Scoring of Atopic Dermatitis Index (SCORAD) at Days 8, 15, 29, 57, 85, 92, 99, 113, 141, and 169 in the Open-LabeleExploratory Study to Evaluate Safety and Efficacy of FB825 in Adults with Atopic Dermatitis.

Subjects showed progressively reduced SCORAD after FB825 administration on Day 1 till approximately Day 55 (approximately 45% reduction). SCORAD score started rising after Day 55 until the second FB825 administration on Day 85 but it is still approximately 30% less compared to baseline. Subjects showed further SCORAD reduction to approximately 55% reduction on Day 113 and maintained the level till the end of study (EOS). (FIG. 7).

(iv) VAS was Reduced Compared to Baseline by FB825

Figure 8:
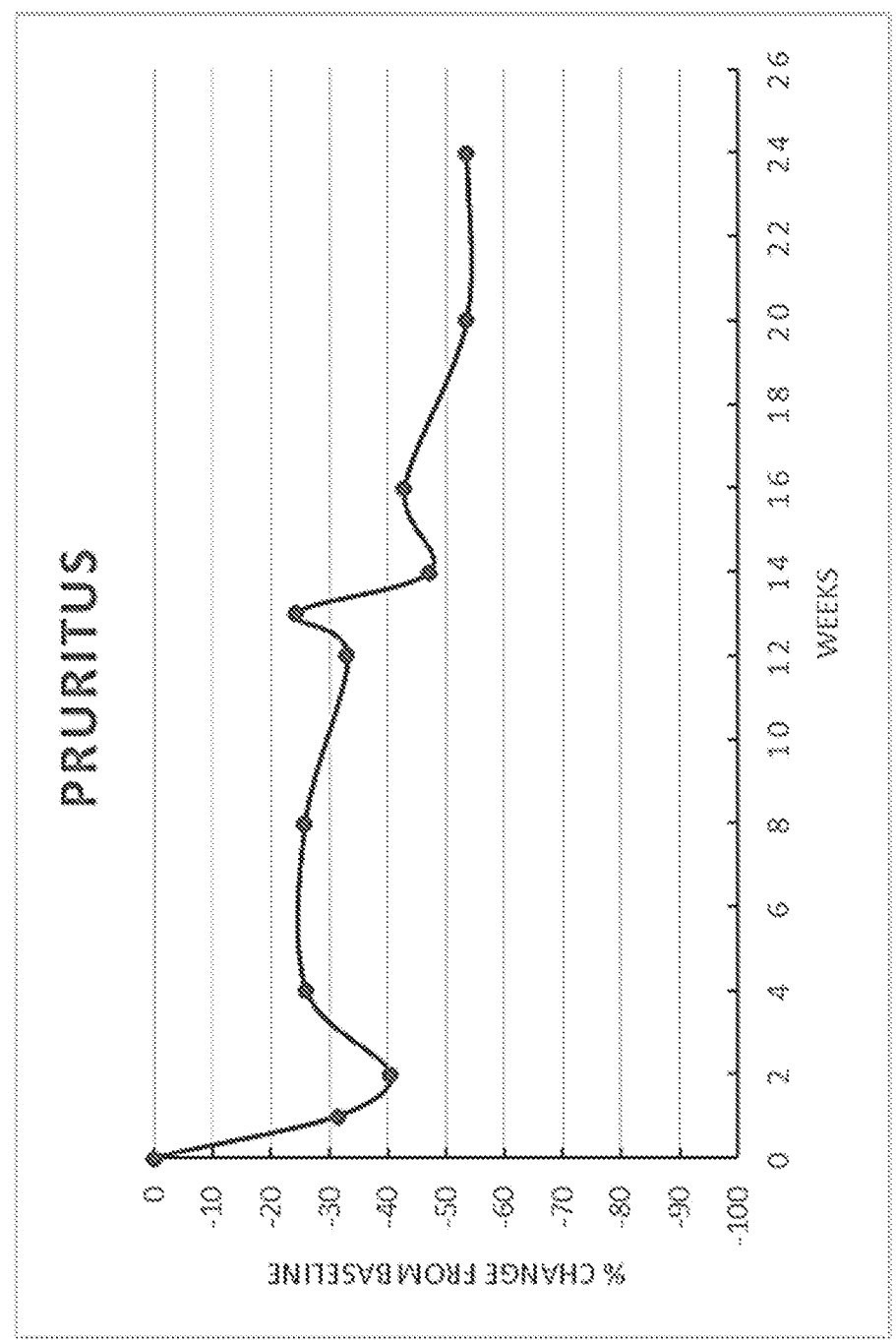
FIG. 8 is a diagram showing the percentage change from baseline in Pruritus Visual Analogue Scale (VAS) at Days 8, 15, 29, 57, 85, 92, 99, 113, 141, and 169 in the Open-LabeleExploratory Study to Evaluate Safety and Efficacy of FB825 in Adults with Atopic Dermatitis.

Subjects showed progressively reduced VAS after FB825 administration on Day 1 till approximately Day 15 (approximately 45% reduction). VAS score started rising after Day 15 and was maintained at 25% reduction compared to baseline until the second FB825 administration on Day 85. Subjects showed further VAS reduction to approximately 55% reduction on Day 113 and maintained the level till the end of study (EOS). (FIG. 8).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating allergic asthma, the method comprising:
(i) administering to a subject in need thereof a first dose of an antibody binding to a Cεmx domain of a membrane-bound IgE; wherein the subject is a human patient having allergic asthma; and
(ii) administering to the subject a second dose of the antibody; wherein the second dose is administered at least 8 weeks and up to 6 months after the first dose; wherein the first dose ranges from 0.5 mg/kg to 15 mg/kg; wherein the antibody comprises a heavy chain variable region, which comprises (a) a heavy chain complementary determining region (CDR) 1, a heavy chain CDR2, and a heavy chain CDR3, and (b) a light chain variable region comprising a light chain CDR1, a light chain CDR2, and a light chain CDR3; and
wherein:
the heavy chain CDR1 comprises the amino acid sequence of residues 26-36 of SEQ ID NO:9;
the heavy chain CDR2 comprises the amino acid sequence of residues 51-66 of SEQ ID NO:9,
the heavy chain CDR3 comprises the amino acid sequence of residues 98-106 of SEQ ID NO:9,
the light chain CDR1 comprises the amino acid sequence of residues 24-39 of SEQ ID NO:10,
the light chain CDR2 comprises the amino acid sequence of residues 55-61 of SEQ ID NO:10; and
the light chain CDR3 comprises the amino acid sequence of residues 94-102 of SEQ ID NO:10.

2. The method of claim 1, wherein the second dose is administered at least 3 months after the first dose.

3. The method of claim 2, wherein the second dose is administered about 12 weeks to about 6 months after the first dose.

4. The method of claim 1, wherein the first dose, the second dose, or both range from 0.5 mg/kg to 15 mg/kg.

5. The method of claim 4, wherein the first dose, the second dose, or both range from 1 mg/kg to 8 mg/kg.

6. The method of claim 1, wherein the first dose, the second dose, or both are administered by intravenous injection.

7. The method of claim 1, wherein the antibody is a human antibody or a humanized antibody.

8. The method of claim 1, wherein the antibody is a full length antibody or an antigen-binding fragment thereof.

9. The method of claim 1, wherein the heavy chain variable region comprises the amino acid sequence of SEQ ID NO: 2, SEQ ID NO:8, or SEQ ID NO:9; and the light chain variable region comprises the amino acid sequence of SEQ ID NO: 3 or SEQ ID NO:10.

10. The method of claim 9, wherein the heavy chain variable region comprises the amino acid sequence of SEQ ID NO:9 and the light chain variable region comprises the amino acid sequence of SEQ ID NO:10.

11. The method of claim 1, wherein the antibody is an IgG1 molecule.

12. The method of claim 1, wherein the antibody comprises a heavy chain comprising the amino acid sequence of residues 20-466 of SEQ ID NO: 11 and a light chain comprising the amino acid sequence of residues 21-239 of SEQ ID NO:12.

13. The method of claim 12, wherein the antibody comprises a heavy chain comprising the amino acid sequence of SEQ ID NO: 11 and a light chain comprising the amino acid sequence of SEQ ID NO: 12.

14. The method of claim 1, wherein the antibody is formulated in a pharmaceutical composition comprising the antibody, a buffer, a salt, and a nonionic surfactant.

15. The method of claim 14, wherein the pharmaceutical composition is an aqueous solution having a pH of 5 to 8.

16. The method of claim 15, wherein the buffer is a histidine buffer, the salt is sodium chloride, and/or the nonionic surfactant is polysorbate 80.

17. The method of claim 16, wherein the antibody in the pharmaceutical composition is about 10 mg/ml to 30 mg/ml, the histidine buffer is of a concentration of about 10 mM to 30 mM, the sodium chloride is of a concentration of about 120 mM to 160 mM, and the polysorbate 80 is of a concentration of about 0.01% to 0.03%.

* * * * *